US008779096B2

(12) United States Patent
Anderson et al.

(10) Patent No.: US 8,779,096 B2
(45) Date of Patent: *Jul. 15, 2014

(54) NEUROGENIN

(75) Inventors: David J. Anderson, Altadena, CA (US);
Quifa Ma, Pasadena, CA (US); Lukas Sommer, Zurich (CH)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/533,279

(22) Filed: Jun. 26, 2012

(65) Prior Publication Data
US 2013/0165385 A1 Jun. 27, 2013

Related U.S. Application Data

(60) Division of application No. 12/941,936, filed on Nov. 8, 2010, now Pat. No. 8,232,076, which is a continuation of application No. 12/024,558, filed on Feb. 1, 2008, now Pat. No. 7,829,308, which is a division of application No. 10/425,259, filed on Apr. 29, 2003, now Pat. No. 7,344,857, which is a continuation of application No. 08/932,411, filed on Sep. 17, 1997, now Pat. No. 6,566,496, which is a continuation of application No. 08/772,009, filed on Dec. 19, 1996, now abandoned, which is a continuation of application No. 08/722,570, filed on Sep. 27, 1996, now Pat. No. 6,555,337.

(51) Int. Cl.
*C07K 14/46* (2006.01)
*C07K 14/47* (2006.01)

(52) U.S. Cl.
USPC ............ 530/350; 530/839; 530/855; 530/300

(58) Field of Classification Search
None
See application file for complete search history.

(56) References Cited

U.S. PATENT DOCUMENTS

| | | | |
|---|---|---|---|
| 6,555,337 | B2 | 4/2003 | Anderson et al. |
| 6,566,496 | B1 * | 5/2003 | Anderson et al. ............. 530/350 |
| 7,344,857 | B2 | 3/2008 | Anderson et al. |
| 7,829,308 | B2 | 11/2010 | Anderson et al. |

FOREIGN PATENT DOCUMENTS

| | | |
|---|---|---|
| AU | 4497297 | 4/1998 |
| CA | 2236419 | 5/1997 |
| CA | 2266422 | 4/1998 |
| EP | 0946720 | 10/1999 |
| WO | 9813491 | 4/1998 |

OTHER PUBLICATIONS

Akasawa et al., "A Mammalian Helix-Loop-Helix Factor Structurally Related to the Product of Drosophila proneural Gene Atonal is a Positive Transcriptional Regular Expressed in the Developing Nervous System", J. Biol. Chem., 270:8730-8738 (1995).
Bartholoma et al., "NEX-1: A Novel Brain-Specific Helix-Loop-Hel x protein with Autoregulation and Sustained Expression in Mature Cortical Neurons", Mech. Devel., 48:217-228 (1994).
Devereux et al., "A Comprehensive Set of Sequence Analysis Program for the VAX", Nucleic Acids Research 12:387-395 (1984).
Jarman et al., "Atonal is a Proneural Gene That Directs Chordotonal Organ Formation in the Drosophila Peripheral Nervous System", Cell, 73:1307-1321 (1993).
Johnson et al., "Two Rat Homologues of Drosphila Achaete-Scute Specifically Expressed in Neuronal Precursors", Nature, 346:858-861 (1990).
Kume et al., "Molecular Cloning of a Novel Basic Helix-Loop-Helix Protein from the Rat Brain", Biochem. Biophys. Res. Commun., 219:526-530 (1996).
Lee et al., "Conversion of Xenopus Ectoderm into Neurons by NeuroD, a Basic Helix-Loop-Helix Protein", Science, 268:836-844 (1995).
Ma et al., "Identification of Neurogenin, a Vertebrate Neuronal Determination Gene", Cell, 87:43-52 (1996).
Naya et al., "Tissue-specific Regulation of the Insulin gene by a Novel Basic Helix-Loop-Helix Transcription Factor", Genes & Dev., 9:1009-1019 (1995).
Reeck et al., ""Homology" in Proteins and Nucleic Acids: A Terminology Muddle and a Way out of it", Cell 50:667 (1987).
Shimizu et al., "Math-2, a Mannalian Helix-Loop-Helix Factor Structurally Related to the Product of Drosophila proneural Gene Atonal, is Specifically Expressed in the Nervous System", Eur. J. Biochem. 229:239-248 (1995).
Smith et al., "Somite Subcomains, Muscle Cell Origins, and the Four Muscle Regulatory Factor Proteins", J. Cell Biol. 127:95-105 (1994).
Snider, "Functions of the Neurotrophins during Nervous System Development: What the Knockouts Are Teaching Us", Cell 77, 627-638 (1994).
Sommer et al., "Neurogenins, a Novel Family of Atonal-Related bHLH Transcription Factors, are Putative Mammalian Neuronal Determination Genes that Reveal Cell Heterogeneity in the Developing CNS and PNS", Molecular and Cellular Neuroscience, 8:221-241 (1996).
Tapscott et al., GenBank, Accession No. U63842 (1996).
Villares et al., "The Achaete-Scute Gene complex of D. melanogaster: Conserved Domains in a Subset of Genes Required for Neurogensis and Their Homology to myc", Cell 50:415-425 (1987).
Rudinger, In Peptide Hormones, ed. J.A. Parsons, University Park Pres, Baltimore, 1976.
Akazawa et al., JBC, vol. 270, p. 8730-8738, 1995.
Gradwohl, et. al., EMBL Database; Mus musculus Math4a; Accession No. Y07621 (date: Aug. 21, 1996).
Gradwohl, et al., EMBL Database; Mus musculus Math4B genomic 1; Accession No. Y09167 (date: Nov. 4, 1996).
McCormick, M.B. et al., "neuroD2 and neuroD3: distinct expression patterns and transcriptional activation potentials within the neuroD gene family," Mole. Cell. Biol., 16(10)5792-5793 (1996).

(Continued)

*Primary Examiner* — Olga N Chernyshev
(74) *Attorney, Agent, or Firm* — Lathrop & Gage LLP; Sean M. Coughlin

(57) ABSTRACT

The invention relates to novel neurogenin proteins, nucleic acids and antibodies.

2 Claims, 20 Drawing Sheets

(56) References Cited

OTHER PUBLICATIONS

Sommer, L. et al., "The cellular function of MASH1 in autonomic neurogenesis," Neuron, 15(6): 1245-1258 (1995).
Turner, D.L. and Weintraub, H., "Expression of achaete-scute homolog 3 in Xenopus embryos converts ectodermal cells to a neural fate," Genes and Dev., 8:1434-1447 (1994).
Examination Report, Application No. EP97943514.6, Date: May 27, 2009.
Examination Report, Application No. EP97943514.6, Date: Oct. 23, 2003.
International Preliminary Examination Report, Application No. PCT/US97/17048, Date: Jan. 12, 1999.
Written Opinion, Application No. PCT/US97/17048, Date: Aug. 27, 1998.
Canadian Office action, Application No. 2266422, Date: Aug. 1, 2007.
Canadian Office action, Application No. 2266422, Date: Jan. 5, 2009.
Examination Report, Application No. EP97943514.6, Date: Mar. 24, 2006.
Weintraub, Cell., 75: 1241-1244 (1993).

* cited by examiner

```
  1  MPAPLETCLSDLDCASSNSGSDLSSFLTDEEDCARLQPLASTSGLSVPAR      neurogenin
  1              MVLLKCE.........YRDEEEDLTSASPCSVTSSFRSPAT   X-NGNR-1a 51  RSAPT......LSGASNVPGGQDEEQER.RRRRGRARVRSEALLHSLRRSR     neurogenin
 33  QTCSSDDEQLLSPTSPGQHQEENSPRCRRSRGRAQGKSGETVLKIKKTR       X-NGNR-1a 95  RVTKANDRERNRMHNLNAALDALRSVTLPSFPDDTKLTKIETLRFAYNYIWA    neurogenin
 83  RVTKANRERNRMHNLNSALDSLREVLPSLPEDAKLTKIETLRFAYNYIWA      X-NGNR-1a 145  LAETLRLADQGLPGGARERLLPPQCVPCLPGPPSPASDTESWGSGAAAS       neurogenin
133  LSETLRLGDPVHRSASTPA.......AAILVQDSSSSQSPSWSCSSSPS       X-NGNR-1a 195  PCATVASPLSDPSSPSASEDFTYGPGGPLFSFPGLPKDLLHTTPCFIPYH      neurogenin
175  SSCCSFSPASPASSTSDSIESWQPSELHLNPFMSASSAFI                X-NGNR-1a
```

FIG._1

|  | < basic >< helix >< loop >< helix-2 > |
|---|---|
| mNeurogenin | RSRRVKANDRERNRMHNLNAALDALRSVLP......SFPD......DTKLTKIETLRFAYNYIWALAET |
| X-NGNR-1a | KTRRVKANNRERNRMHNLNSALDSLREVLP......SLPE......DAKLTKIETLRFAYNYIWALSET |
| mNeuroD/BETA2 | KLRRMKANARERNRMHGLNAALDNLRKVVP......CYSK......TQKLSKIETLRLAKNYIWALSEI |
| mNex1/Math2 | KFRRQEANARERNRMHGLNDALDNLRKVVP......CYSK......TQKLSKIETLRLAKNYIWALSEI |
| rKW8 | KLRRQKANARERNRMHDLNAALDNLRKVVP......CYSK......TQKLSKIETLRLAKNYIWALSEI |
| mMath1 | KNRRLAANARERRRMHGLNHAFDQLRNVIP......SFNN......DKKLSKYETLQMAQIYINALSEI |
| D.Atonal | RKRRLAANARERRRMQNLNQAFDRLRQYLP......CLGN......DRQLSKHETLQMAQTYISALGDL |
| rMash1 | VARR...NERERNRVKLVNLGFATLREHVP..........NG......AANKKMSKVETLRSAVEYIRALQQL |
| D.AS-C T5 | VIRR...NARERNRVKQVNNGFSQLRQHIPAAVIADLSNGRRGIGPGANKKLSKVSTLKMAVEYIRRLQKV |

*FIG._2*

```
  1  ATCCGGAGCT GATCTGATCG CCGGCGACAT CAGTCGGGAG ACCAGCCCGG
 51  CGCGTGGCCC CCTGCAGGCG AGGCGAGGAG GCCAAGCCCA TTCCCTCCCT
101  GAGCCCCTGC GATCTTCCCC GGCCCTCGCG CCTGCAGCAG GCACAGGCTA
151  GCCCCGGGTC ATACGGACAG TAAGTGCGCT TCGAAGGCCG TGCACTCGGC
201  CCACATTCAA GCCCTCCAAA CCTCCCGTCC GTCCGTCCGT CCTGCAACGA
251  TGCCTGCCCC TTTGGAGACC TGTCTCTCTG ACCTCGACTG CGCCAGCAGC
301  AACAGCGGGA GCGACCTGTC CAGTTTCCTC ACCGACGAGG AGGACTGTGC
351  CAGGCTCCAG CCCCTAGCTT CCACCTCAGG GCTGTCCGTG CCAGCCCGCA
401  GGAGCGCGCC CACCCTCTCC GGGGCATCGA ACGTTCCCGG TGGCCAGGAC
451  GAAGAGCAGG AGCGGCGGCG ACGGCGAGGT CGCGCGCGGG TGCGGTCCGA
501  GGCGCTGCTG CACTCGCTGC GGAGGAGCCG TCGGCGTCAAG GCCAACGATC
551  GCGAGCGCAA CCGTATGCAT AACCTCAACG CTGCGCTGGA CGCTCTGCGC
601  AGCGGTGCTGC CCTCGTTCCC CGACGACACC AAGCTCACCA AGATTGAGAC
651  GCTGCGCTTC GCCTACAAACT ACATCTGGGC CCTGGCTGAG ACACTGCGCC
701  TGGCAGATCA AGGGCTCCCG GGGGGCGGTG CCCGGGAGCG CCTCCCTGCCT
```

FIG._3A

```
 751   CCGCAGTGTG TCCCCTGCCT GCCCGGTCCC CCGAGCCCGG CCAGCGATAC
 801   AGAGTCCTGG GGCTCCGGGG CCGCTGCCTC CCCCTGCGCT ACTGTGGCGT
 851   CACCACTCTC TGACCCCAGT AGTCCCCTCGG CTTCAGAAGA CTTCACCTAT
 901   GGCCCGGGTG GTCCCCTTTT CTCCTTTCCT GGCCTGCCCA AAGACCTCCT
 951   CCATACGACA CCCTGCTTCA TCCCGTACCA CTAGGGCTTT GCAAGACAAC
1001   GTTAATACTT CTTTCCTGCC CCAGTCTATG AGCAATAGAT GGGGGAGCCG
1051   GCTGAAGCCT CGGGAGCAC CCTTACCCCC AGGTTGGATGC TGGGAGCTTT
1101   AAAGAGGGGA GGGATACCTG ACCACTTGCT AGGTTGCCGC ACCCTCGCTG
1151   AGAAGCTGCC CCTCGGACTG TTTCCCCACG CCCCAGCACC GGGCCCCTCC
1201   TGCCCCGCCCC CCAGACGGGC TTTCGGTTTT TTTTTTTGGAC TTCCTGAACT
1251   TCACAAAAACC TCCTTTGTGA CTGGCTCAGA ACTGACCCCA GCCACCACTT
1301   CAGTGTGATT TGGAAAAGGG ACAGATGAGC CCCTGAAGAC GAGGTGAAAA
1351   GTCAATTTTA CAATTTGTAG AACTCTAATG AAGAAAAACG AGCATGAAAA
1401   TTCGGTTTGA GCCGGCTGAC AATACAATGA AAAGCTTAA  AAAAAGGAG
1451   ACACAAGGAG TGGGCTTCAT GCATTATGGA TCCCGACCCC CACCACTGTG
1501   GGCTTGCTCC CGGAAGAACT GAGTGCT
```

*FIG._3B*

```
  1 ATGCCTCCCC CTTTGGAGAC CTGCATCTCT GATCTCGACT
 41 GCTCCAGCAG CAACAGCAGC AGCGACCTGT CCAGCTTCCT CACCGACGAG
 91 GAGGACTGTG CCAGGCTACA GCCCCTAGCC TCCACCTCGG GGCTGTCCGT
141 GCCAGCCCGG AGGAGCGCTC CCGCCCTCTC CGGGGCATCG AATGTTCCCG
191 GTGCCCAGGA CGAAGAGCAG GAACGGCGGA GGCGGCGAGG TCGCGCTCGG
241 GTGCGGTCCG AGGCTCTGCT GCACTCCCTG CGGAGGAGTC GTCGCGTCAA
291 AGCCAACGAT CGCGAGCGCA ACCGCATGCA CAACCTCAAC GCTGCGCTGG
341 ACGCCTTGCG CAGCGTGCTG CCCTCGTTCC CCGACGACAC CAAGCTCACC
391 AAGATTGAGA CGCTGCGCTT CGCCTACAAC TACATCTGGG CCCTGGCTGA
441 GACACTGCGC CTGGCAGATC AAGGGCTCCC CGGGGGCAGT GCCCGGGAGC
491 GCCTCCTGCC TCCGCAGTGT GTCCCCTGTC TGCCCGGGCC CCCGAGCCCG
541 GCCAGCGACA CTGAGTCCTG GGGTTCCGGG GCCGCTGCCT CCCCCTGCGC
591 CACTGTGGCA TCACCACTCT CTGACCCCAG TAGTCCCTCG GCTTCAGAAG
641 ACTTCACCTA TGGCCCGGGC GATCCCCTTT TCTCCTTTCC TGGCCTGCCC
691 AAAGACCTGC TCCACACGAC GCCCTGTTTC ATCCCATACC ACTAGTAA
```

FIG._4

```
  1  GCGTGTCACA CGGCAGTTGC ACTCATAATA CACTGTGAGC TGACAGTCGC
 51  AACCACGCCC GACAGGGAAC ACGCAGCAAG TCTACTGCAC GACTATAACC
101  CGACGACTCG ACCCAACTCA CCTGCTGCTT CAGGGGCCAA ACACCAAGTT
151  ATAAAGTAAG TAACTTCCAT TGCAACTGCA GCATTGTCAC TTGCGACAGC
201  GCATGAAGTA GTGAGAGGCA CAGACCATGT ACATATATGG GGTTTGTGGT
251  TATTATAGTA AGTGGGATGA TGTTTGGGTT ATTATAGTAA GTGGATGTGA
301  AGTTGTCAGT GCAACATTGG GGCTAACCAT TGGCTGTGTG TTTGCGCTTG
351  TCTAGGATGG TGCTGCTCAA GTGCGAGTAC CGCGATGAAG AGGAGGACCT
401  GACCCTCTGCC TCCCCCTGCT CCGTGACCTC CTCTTTCCGT TCCCCGGCGA
451  CGCAGACGTG CAGCTCGGAC GATGAGCAGC TCCTGAGTCC CACCAGCCCG
501  GGACAGCACC AGGGGGAAGA GAACAGCCCG CGATGCAGGA GGAGCCGAGG
551  CCGCGCTCAG GGCAAGAGCG GAGAAACTGT GTTAAAGATC AAGAAGACCC
601  GGCGCGTTAA AGCTAACAAC CGGGAAAGGA ATCGCATGCA CAACCTGAAC
651  TCTGCGCTTG ATTCCCTCAG GGAAGTGTTG CCCTCTTTAC CTGAAAGATGC
701  CAAAACTCACC AAGATAGAGA CCTTGCGCTT TGCCTACAAC TACATCTGGG
```

FIG. 5A

```
 751   CTCCTTAGCGA AACTTTGCGC CTTGGGCGACC CAGTGCACCG ATCTGCTTCC
 801   ACCCCAGCAG CAGCCATATT GGTGCAGGAC TCCTCTTCAT CCCAGAGCCC
 851   CTCCTGGAGC TGCAGCTCGT CCCCTTCTTC CTCTTGTTGC TCCTTCTCCC
 901   CGGCCAGCCC TGCCAGCTCC ACCTCGGACA GTATTGAGTC CTGGCAGCCC
 951   TCTGAGCTCC ACCTGAAACCC CTTCATGTCT GCCAGCAGCG CTTTCATTTG
1001   AACTCCTGTT GGACTATGAT GGATTCTCAC ACTTCCAATT GCTACATATG
1051   AAGAATACCT CAGTGGGGCC CCAGTGCAAA TGATTTTCCT GGGAACCCAG
1101   TTTATTGAGC ATGAGCCCAT ATAGTGTAAT AATATCATCC TGCAGTGACC
1151   AAATTGCACT CTGTGGGTTC TGCTGATGGG GAGAAGTGGG GGGCTTGATC
1201   CCCCTGAGTT TGTGCTTACC TGTATAGCAT TTACTCCCCC TGCTGTCATG
1251   CCCCTGGCAT ATGATGGAGT ACATTGCTGG GTCTATTTTA TTATCAGCAA
1301   TGTGAACTGA AA
```

*FIG._5B*

```
  1  CGAGTGCGCA ACACTTGAGC TGGAGTGCGG GGCGGTGTC ACACACACAC
 51  TGAACTGCCA CTGACACCAG AGACACAGCG AGTGGGAACC CCCTGCTACT
101  ACAGGACTAG GAGAAAAGCC GCACAGCCTG CAGCGCCCGCA ACCCGACTCA
151  CCTGCTGCTC CCGGAGCCAC AAGCCTGGCG CACAAGATGG TGCTGCTGAA
201  GTGCGAATAC CGCGATGAGG TGTCGGAACT GACCTCTGTC TCCCCCTGCT
251  CCGTGTCCTC CTCCCTCTTCA CACCCGTCCC CGGCGATGCA GACGTGCAGC
301  TCGGACGATG AGCAGCTACA CAGTCCGACA AGCCCGACGC TCACGCACCT
351  GCAGCAGGGA CGGGACCAGG GGGAGGAGAA CAGCCCGCGA TGCAGGAGGA
401  GCCGAGCCCG CGGAGACACC GTGCTGAAGA TCAAGAAGAC CCGGCGCGTT
451  AAAGCCAATA ACCGCGAGAG GAATCGCATG CACCACCTGA ACTATGCGCT
501  CGATTCTCTG AGGGAGGTTC TACGTCATT ACCCGAAGAC GCCAAACTCA
551  CCAAGATAGA GACCTTGCGC TTTGCCCACA ACTACATCTG GGCTCTTTAGC
601  GAAACTTTGC GCCTGGGCCGA CCAGCTGCAC GGATCTACTT CCACCCCAGC
651  AGCAGCCATA TTGGTACAGG ACTCCTATCC TTCCCTGAGC CCCTCCTGGA
701  GCTGCAGCTC GTCCCCATCC TCCAACTCTT GCGACTCCTT CTCCCCGACC
```

FIG._6A

| | | | | |
|---|---|---|---|---|
| 751 | AGCCCTGCCA | GCTCCACCTC | GGACAGTATT | GAGTACTGGC | AGCCCTCTGA |
| 801 | GCTCCGCTTG | AACCCCTTCA | TGTCTGCCCT | TTGAACGCAC | AGGACTATGG |
| 851 | GTGATTTTAA | CTTTTTACAC | TTTAAATTCC | TGCTTCCCAT | AAGGGTCAAG |
| 901 | TACTGCAGGG | GTTACATATC | AAGTTTACCT | CAGGGGGGGC | CACAGCAAAT |
| 951 | TCTTTTCCTG | GGCCCTAAAA | TGTCCTCTGA | ATTTGAGCCC | ATATAGTGCA |
| 1001 | ATGGTATAAC | CCTGCAATGG | TATAATCCAG | CAATGGTATA | ATCCTGCATC |
| 1051 | GTTACCTAAT | TGTACTTTGT | GGGGTCTGCT | GATGGGGGAC | AAGTGTTTGA |
| 1101 | CCTGTGTCCA | GAGTTTCACA | TTTACTCCCC | CTTTTGGTAT | ATCTCTGGCC |
| 1151 | GCAACACTTG | CTGTGTCTGT | TTCATCGTTA | GCTATGTGTA | TTAGGAAACT |
| 1201 | GTCTATCCCT | CATCTGCACC | TGTTAGACTA | CAGCTACCAA | CTTCCTGTTA |
| 1251 | CCAGGGGGCT | ACTGGGTAAT | GTACTTC | | |

*FIG._6B*

```
  1   CTTAGGAAGCGGCCAAGCCGGCGGAGCGGAGGACACCGTGCTCGGTTCCGGGTGGGGACA
      ----+----|----+----|----+----|----+----|----+----|----+----|   60
      GAATCCTTCGCCGGTTCGGCCGCCTCGCCTCCTGTGGCACGAGCCAAGGCCCACCCCTGT

61   TTCCCGGACACACCGGAGCAGCTGGCGCCGAACATTGGAGCCGGTAGTAAGTG
      ----+----|----+----|----+----|----+----|----+----|----+----|  120
      AAGGGCCTGTGTGTGGCCTCGTCGACGGCCTTGTAACCTCGGCGCATCCATTCAC

121   TGCATGCCGCGGCTTTCCATTCGCAGGCAGTGTCCCACGCAGGCTCACGCGCCCAGCC
      ----+----|----+----|----+----|----+----|----+----|----+----|  180
      ACGTACGGCGCCGAAAGGTAAGCGTCCGTCACAGGGTGCGTCCGAGTGCGGCGGGTGCG

181   TAACTCCATCGTTTAGACGCAGTGACTTCTGTGACCGGCAGAAGGTGGCTCGAGCCCGGG
      ----+----|----+----|----+----|----+----|----+----|----+----|  240
      ATTGAGGTAGCAAATCGCTCACTGAAGACACTGGCCGTCTTCCACCGAGCTCGGGCCC

241   GCGCTCCTCCCCCAGCTCTGTCCTCGCCATCTTCGCCGAATGCACATTGAGGAGATGGAGG
      ----+----|----+----|----+----|----+----|----+----|----+----|  300
      CGCGAGGAGGGGTCGAGACAGGAGCGGTAGAAGCGCTTACGTGTAACTCCCTCTACCTCC

301   GGGGGGGGCGGGGGCCCCGGCGCCGCCGTGCTGTGAAATGGGACAGTAAGACCCTTATTTAAAG
      ----+----|----+----|----+----|----+----|----+----|----+----|  360
      CCCCCCCCGCCCCCGGGGCCGCGGCGGCACGACACTTTACCCTGTCCATTCTGGAATAAATTTC
```

FIG._7A-1

```
361  ATCTGCCTCTCTTTCTCAGGATGTTCGTCAAATCTGAGACTCTGGAGTTGAAGGAGGAA  420
     ----+---------+---------+---------+---------+---------+
     TAGACGGAGAAGAAAGAGTCCTACAAGCAGTTTAGACTCTGAGACCTCAACTTCCTCCTT
                     M  F  V  K  S  E  T  L  E  L  K  E  E

421  GAGGAGGTACTGATGCTGCTGGGCTCGGCTTCCCGGCTCGGCTCCCGGCGACCCTGACCCCGATG  480
     ----+---------+---------+---------+---------+---------+
     CTCCTCCATGACTACGACGACCCGAGCCGAAGGGCCGAGCCGAGCCGAGCCGCTGGGACTGGGGCTAC
      E  E  V  L  M  L  L  G  S  A  S  P  A  S  A  T  L  T  P  M

481  TCCTCCAGCGCGGACGAGGAGGAGGACGAGGAGCTGCCGCCGCCGGGGCTCCGCGTGGGG  540
     ----+---------+---------+---------+---------+---------+
     AGGAGGTCGCGCCTGCTCCTCCTCCTGCTCCTCGACGGCGGCGGCCCCGAGGGCGGCACCC
      S  S  S  A  D  E  E  E  D  E  E  E  L  R  R  P  G  S  A  R  G

541  CAGCGTGGAGCGGAAGCCGAGCAGGGGTGCAGGGCAGTCCGGGTCGGGTGCCGGGGGT  600
     ----+---------+---------+---------+---------+---------+
     GTCGCACCTCGCCTTGGCTCGTCCCCCACGTCCCGTCAGGCCGCAGCCCACGGCCCCA
```

FIG._7A-2

```
      Q   R   G   A   E   A   E   Q   G   V   Q   Q   G   S   P   A   S   G   A   G   G
    TGCCGGCCAGGGCGGCTGCTGGGCCTGATGCACGAGTGCAAGCGTCGCCCGTCGCGCTCA
601 ------+---------+---------+---------+---------+---------+ 660
    ACGGCCGGTCCCGCCGACGACCCGGACTACGTGCTCACGTTCGCAGCGGGCAGCGCGAGT

C   R   P   G   R   L   L   G   L   M   H   E   C   K   R   R   P   S   R   S
    CGGGCCGTCTCCCGAGTGCCAAGACGGCGGAGACGGTGCAGGCGCATCAAGAAGACCCGC
661 ------+---------+---------+---------+---------+---------+ 720
    GCCCGGCAGAGGGCTCCACGGTTCTGCCGCCTCTGCCACGTCGCGTAGTTCTTCTGGGCG

R   A   V   S   R   G   A   K   T   A   E   T   V   Q   R   I   K   K   T   R
    AGGCTCAAGGCCAACAACCGGAGCGCATGCACGAACCTAAACGCCGGCGCTGGAC
721 ------+---------+---------+---------+---------+---------+ 780
    TCCGAGTTCCGGTTGTTGGCCTCGCGTTGCGTAGTGTTGGATTTGCGGCCGCGACCTG

R   L   K   A   N   N   R   E   R   N   R   M   H   N   L   N   A   A   L   D
    GCGCTGCCGCGAGGTGCTGCCCCACCTTCCCGAGGATGCCAAGCTCACGAAGATCGAGACG
781 ------+---------+---------+---------+---------+---------+ 840
    CGGCGACGGCGCTCCACGACGGGGTGGAAGGGCTCCTACGGTTCGAGTGCTTCTAGCTCTGC

A   L   R   E   V   L   P   T   F   P   E   D   A   K   L   T   K   I   E   T
    CTGGCCTTCGCCCACAATTACATCTGGGCGCTCACCGAGACTCTGCGCCTGGACCAC
841 ------+---------+---------+---------+---------+---------+ 900
    GACGCGAAGCGGGTGTTAATGTAGACCCGCGAGTGGCTCTGAGACGCGGACCGCCTGGTG
```

*FIG._7B-1*

```
     L  R  F  A  H  N  Y  I  W  A  L  T  E  T  L  R  L  A  D  H  ;
     TGCGCCGGCGCCGGTGGCCTCCAGGGGCCGCTCTTCACGGAGACGGTGCTCCTGAGCCCG
901  ------------+------------+------------+------------+------------+------------+  960
     ACGCGGCCGCGGCCACCGGAGGTCCCCGGCGAGAAGTGCCTCTTCACCACGAGGACTCGGGC

C  A  G  G  G  L  Q  G  A  L  F  T  E  A  V  L  L  S  P  ;
     GGAGCTGCGCTCGGCGCCAGGGGACAGCCCCTTCTCCACCTTCTCCTGAGCTGCACC
961  ------------+------------+------------+------------+------------+------------+  1020
     CCTCGACGCGAGCCGCGGTCCCCCTGTCGGGGAAGAGGTGAAGGAGGACCTGACGTGG

G  A  A  L  G  A  S  G  D  S  P  P  P  S  S  W  S  C  T  ;
     AACAGCCCGGGCGTCATCCTCCAACTCCAGTCCCCATACAGCTGCACTTTATGCCCGCT
1021 ------------+------------+------------+------------+------------+------------+  1080
     TTGTCGGGCCCAGTAGGAGGTTGAGGTCAGGGGTATGTCGACGTGAAATAGCGGGCGA

N  S  P  A  S  S  S  N  T  S  P  Y  S  C  T  L  S  P  A  ;
     AGCCCCGGGGTCAGACGTGACTACTGGCAGCCCCACCTCCGGAGAAGCATCGTTATGCG
1081 ------------+------------+------------+------------+------------+------------+  1140
     TCGGGGCCCAGTCTGCACCTGATGACCGTCGGGGGTGAGGCCCTCTTCGTAGCAATACGC

S  P  G  S  D  V  D  Y  W  Q  P  P  P  P  E  K  H  R  Y  A  -
     CCTCACCTGCCCCTGCCCGGACTGTATCTAGAGCTGCGGGTCCCCTCTCTGTCTCC
1141 ------------+------------+------------+------------+------------+------------+  1200
```

FIG._7B-2

```
            GGAGTGGGACGGGGAGCGGTCCCTGACATAGATCTCGACGCCCAGAGGGAGAGAGACAGAGG
             P   H   L   P   L   A   R   D   C   I   *

TACCCGGGCCCCTCCTTCCATCCTTCTCCCGCCCCCAACCCTCCAGCCCCGGAATCCAC
     1201   --------+---------+---------+---------+---------+---------+  1260
            ATGGGCCCGGGGAGGAAGGGTAGGAAGAGGGCGGGGTGGAGGTGCGGGGCCTTAGGTG

TTCACAGAACAGAAGTTGGCCCTTTGCAATCCCCTCCGCGCTGTGCTTCGGGGGTTGG
     1261   --------+---------+---------+---------+---------+---------+  1320
            AAGTGTCTTGTCTTCAACCGGGAAACGTTAGGGGAGGCGCGACACGAAGCCCCCAACC

AAAACAACTCTGTTTATTGAAATTAAGATTTTGGTCAAAAAGAATATGCTTTTTGAAT
     1321   --------+---------+---------+---------+---------+---------+  1380
            TTTTGTTGAGACCAAATAACTTTAATTCTAAAACCAGTTTTTCTTATACGAAAAACTTA

TGGGG
     1381   -----  1385
            ACCCC
```

FIG._7C

NEUROGENIN2

1    MFVKSETLEL KEEEEVLMLL GSASPASATL TPMSSSADEE EDEELRRPGS

51   ARGQRGAEAE QGVQGSPASG AGGCRPGRLL GLMHECKRRP SRSRAVSRGA

101  KTAETVQRIK KTRRLKANNR ERNRMHNLNA ALDALREVLP TFPEDAKLTK

151  IETLRFAHNY IWALTETLRL ADECAGAGGL QGALFTEAVL LSPGAALGAS

201  GDSPSPPSSW SCTNSPASSS NSTSPYSCTL SPASPGSDVD YWQPPPPEKH

251  RYAPHLPLAR DCI*

*FIG._8*

```
  1  ATTCTTTGAGTCGGGAGAACTAGGTAACAATTCGAAACTCCAAAGGGTGATGAGGG   60
     ----------+---------+---------+---------+---------+---------+
     TAAGAAACTCAGCCCTCTTGATCCATTGTTAAGCCTTTGAGGTTTCCACTACTCCCC

61  CGGCGGGGGTGTGTGGGGATACTCTGGTCCCCGTGCAGTGACCTCTAAGTCAGAGG  120
     ----------+---------+---------+---------+---------+---------+
     GCGCGCCCCACACACCCCTATGAGACCAGGGGCACGTCACTGGAGATTCAGTCTCC

121  CTGGCACACACACACCTTCCATTTTTCCCAACCGCAGGATGGCGCCTCATCCCTTGAT  180
     ----------+---------+---------+---------+---------+---------+
     GACCGTGTGTGTGTGGAAGTAAAAAGGTTGGCGTCCTACCGCGAGTAGGAACCTA
                                    M   A   P   H   P   L   D   -

181  GCGCTCACCATCCAAGTGTCCCCAGAGACAACAAACCTTTTCCCGGAGCCTGGACCAC  240
     ----------+---------+---------+---------+---------+---------+
     CGCGAGTGGTAGTTCACAGGGGTCTCTGTTGTTGGAAAAGGGCCTCGGAGCCTGGTG
      A   L   T   I   Q   V   S   P   E   I   Q   Q   P   F   P   G   A   S   D   H   -

241  GAAGTGCTCAGTTCCAATTCCACCCCACTAGCCCCACTCTCATACCTAGGGACTGCTCC  300
     ----------+---------+---------+---------+---------+---------+
     CTTCACGAGTCAAGTTAAGGTGGGGTGATCGGGGTGAGAGTATGGATCCCTGACGAGG
      E   V   L   S   S   N   S   T   P   P   S   P   T   L   I   P   R   D   C   S   -
```

FIG._9A-1

```
301  GAAGCAGAAGTGGGTGACTGCCCGAGGGACCTGCGAGGAAGCTCCGCGGCCCGACGCGGAGGG
     ----+----+----+----+----+----+----+----+----+----+----+----+ 360
     CTTCGTCTTCACCCACTGACGGCTCCCTGGAGCGCTCCTTCGAGGCGCCGGGCTGCGCCTCCC

E  A  E  V  G  D  C  P  R  G  T  S  R  K  L  R  A  R  R  G  G  -

361  CGCAACAGGCCCAAGAGAGCGAGTTGGCACTCAGCAAACAGCGAAGAAGCCGGCGCAAGAAG
     ----+----+----+----+----+----+----+----+----+----+----+----+ 420
     GCGTTGTCCGGGTTCTCTCGCTCAACCGTGAGTCGTTTGTCGCTTCTTCGGCCGCGTTCTTC

R  N  R  P  K  S  E  L  A  L  S  K  Q  R  R  S  R  R  K  K  -

421  GCCAATGATCGGGAGCGCAATGCACAACCTCAACTCGGCGCTGGATGCGCTGCGC
     ----+----+----+----+----+----+----+----+----+----+----+----+ 480
     CGGTTACTAGCCCTCGCGTTAGCGTGTTGGAGTTGAGCCGCGACCTACGCGACGCG

A  N  D  R  E  R  N  R  M  H  N  L  N  S  A  L  D  A  L  R  -

481  GGTGTCCTGCCCACCTTCCCGGATGACGCCAAACTTACAAAGATCGAGACCCTGCGCTTC
     ----+----+----+----+----+----+----+----+----+----+----+----+ 540
     CCACAGGACGGGTGGAAGGGCCTACTGCGGTTTGAATGTTTCTAGCTCTGGGACGCGAAG
```

FIG.-9A-2

```
            G  V  L  P  T  F  P  D  D  A  K  L  T  K  I  E  T  L  R  F    -
      GCCCACAACTACATACTGGGCACTGACTCAGAGGCTGCGCATAGCGGACCACAGCTTCTAT
541   ------+---------+---------+---------+---------+---------+   600
      CGGGTGTTGATGTAGACCCGTGACTGAGTCTCGACGCGTATCGCCTGGTGTCGAAGATA

A  H  N  Y  I  W  A  L  T  Q  T  L  R  I  A  D  H  S  F  Y    -
      GGCCCGGAGCCCCCTGTGCCCTGTGAGAGCTGGAGAGCCCCGGAGTGGCTCCAACGGG
601   ------+---------+---------+---------+---------+---------+   660
      CCGGGCCTCGGGGACACGGGACACCTCTCGACCCTCTCGGGGCCTCCACCGAGTTGCCC

G  P  E  P  P  V  P  C  G  E  L  G  S  P  G  G  G  S  N  G    -
      GACTGGGGCCTCTATCTCCCCAGTCTCCCAAGCGGGTAACCTGAGCGGGCCCCACGGGCCTCA
661   ------+---------+---------+---------+---------+---------+   720
      CTGACCCCGAGATAGAGGGTCAGAGGGTTCGCCCATTGGACTCGCCGGGTGCCGGAGT

D  W  G  S  I  Y  S  P  V  S  Q  A  G  N  L  S  P  T  A  S    -
      TTGGAGGAATTCCCTGGCCTGCAGGTGCCCAGCTCCCATCCTATCTGCTCCCGGGAGCA
721   ------+---------+---------+---------+---------+---------+   780
      AACCTCCTTAAGGGACCGGACGTCCACGGGTCGAGGGGTAGGATAGACGAGGGCCCTCGT

L  E  E  F  P  G  L  Q  V  P  S  S  P  S  Y  L  L  P  G  A    -
      CTGGTGTTCTCAGACTTCTGTGA
781   ------+---------+------   804
      GACCACAAGAGTCTGAAGAACACT

NEUROGENIN3

1    MAPHPLDALT IQVSPETQQP FPGASDHEVL SSNSTPPSPT LIPRDCSEAE
51   VGDCRGTSRK LRARRGGRNR PKSELALSKQ RRSRRKKAND RERNRMHNLN
101  SALDALRGVL PTFPDDAKLT KIETLRFAHN YIWALTQTLR IADHSFYGPE
151  PPVPCGELGS PGGGSNGDWG SIYSPVSQAG NLSPTASLEE FPGLQVPSSP
201  SYLLPGALVF SDFL*

NEUROGENIN2 x Xenopus NGNR-1a

```
  1  .MFVKSETLELKEEEEVLMLLGSASPASATLTPMSSSAD..EEEDEELRR  47
      :::|:   |  :::|||   |  ||||| | |    |    :  :||:|
  1  MVLLKC...EYRDEEED...LTSASPCSVTSSFRSPATQTCSSDDEQLLS  44

48  PGSARGQRGAEAEQGVQGSPASGAGGCRPGRLLGLMHECKRRPSRSRAVS  97
      | |: : ||                                :  : |||:||
 45  PTSPGQHQGEE......................NSPRCRRSRGRA..  67

98  RGAKTAETVQRIKKTRRLKANNREPNRMHNLNAALDALREVLPTPPEDAK  147
      :| :|||  :|||||||||||||||||||||||| |||  ||||| |||
 68  .QGKSGETVLKIKKTRRVKANNREPNRMHNLNSALDSLREVLPSLPEDAK  116

148  LTKIETLRFAHNYIWALTETLRLADHCAGAGGLQGALFTEAVLLSPGAAL  197
      ||||||||||||||||||||||| :|    ::             |:|||
117  LTKIETLRFAYNYIWALSETLRLGDPVHRSAS..........TPAAAI  154

198  GASGDSPSPPSWSCTNSPASSSNSTSPYSCTLSPASPGSD.VDYWQPPP  246
      : ||    |||| || ||: | ||    |||| || :: |||
155  LVQDSSSSQSPSWSCSSSPSSSCCSFSP....ASPASSTSDSIESWQPS.  199

247  PEKHRYAPHLPLARDCI*  264
      :   |  :        ||
200  ..ELHLNPFMSASSAFI*  215
```

NEUROGENIN

RELATED APPLICATIONS

This application is a divisional application of U.S. patent application Ser. No. 12/941,936, filed Nov. 8, 2010, which is a continuation application of U.S. patent application Ser. No. 12/024,558, which is a divisional application of U.S. patent application Ser. No. 10/425,259, filed Apr. 29, 2003 which is a continuation of U.S. patent application Ser. No. 08/932,411, filed on Sep. 17, 1997, which is a continuation of U.S. patent application Ser. No. 08/772,009, filed on Dec. 19, 1996; which is a continuation of U.S. patent application Ser. No. 08/722,570, filed Sep. 27, 1996. The contents of these applications are incorporated herein by reference in their entirety.

FIELD OF THE INVENTION

The invention relates to novel neurogenin proteins, nucleic acids and antibodies.

BACKGROUND OF THE INVENTION

Transcription factors in the basic-helix-loop-helix (bHLH) family have been shown to play a central role in cell type determination, in several tissues and organisms. For example, MyoD and myf5 are necessary and sufficient for mammalian myogenesis, while the proneural genes achaete-scute and atonal perform similar functions during Drosophila neurogenesis (for reviews, see (Weintraub, 1993, Cell. 75, 1241-1244; Jan and Jan, (1994) Ann. Rev. of Genet. 28, 373-393.). In both vertebrate myogenesis and fly neurogenesis, multiple functionally-interchangeable bHLH proteins act in networks and/or cascades within their respective lineages (Jan and Jan, 1993). For example, at least four different bHLH proteins are sequentially expressed during murine muscle development: MyoD/myf5; myogenin and MRF4 (Olson and Klein, 1994). Similarly in Drosophila expression of achaete-scute is followed by that of asense during peripheral neurogenesis (Brand et al., 1993; Dominguez and Campuzano, 1993; Jarman et al., 1993a). The function of such cascades is not yet clear, although it has been suggested that the later-acting genes function in differentiation rather than in determination (Weintraub, 1993; Lee et al., 1995). Although numerous bHLH proteins expressed during vertebrate neurogenesis have been identified (Johnson et al., 1990; Akazawa et al., 1992; Ferreiro et al., 1992; Sasai et al., 1992; Ishibashi et al., 1993; Turner and Weintraub, 1994; Akazawa et al., 1995; Lee et al., 1995; Shimizu et al., 1995), none so far examined exhibits the functional properties expected of a neuronal determination factor ((Guillemot et al., 1993; Sommer et al., 1995); see below).

One feature that characterizes the proneural genes in Drosophila is their interaction with the genetic circuitry underlying lateral inhibition. Lateral inhibitory interactions between neuroectodermal cells, mediated by the products of the neurogenic genes Notch and Delta, result in the selection of a single sensory organ precursor (SOP) cell from a group of developmentally equivalent undetermined cells called a "proneural cluster" (Ghysen et al., 1993). All cells in the proneural cluster initially express achaete-scute, but during the selection process proneural gene expression becomes restricted at high levels to the SOP (Cubas et al., 1991). This restriction occurs because the proneural genes promote expression of Delta (Hinz et al., 1994; Kunisch et al., 1994), and their expression and function are in turn inhibited by signalling through Notch (for review, see (Ghysen et al., 1993)). Thus, cells which express sufficient achaete-scute, and hence Delta, to inhibit proneural activity in their neighbors adopt an SOP fate (for discussion, see (Chitnis, 1995)). In this way, the proneural genes both promote a neural fate cell-autonomously, and inhibit this fate non-autonomously.

Lateral inhibition mediated by vertebrate homologs of Notch and Delta has recently been demonstrated to regulate primary neurogenesis in Xenopus (Chitnis et al., 1995). Primary neurons differentiate in three parallel rows within the neural plate; between these rows undifferentiated neural plate cells are set aside for later waves of neurogenesis. Expression of X-Delta-1 defines three broader longitudinal domains that prefigure these territories of primary neurogenesis. Ectopic expression of a dominant negative form of X-Delta-1 (X-Delta-1$^{Stu}$) increases the density of neurons that differentiate within each territory, but does not increase the width of each territory or the overall area of the neural plate (Chitnis et al., 1995). Conversely, expression of constitutively active forms of X-Notch-1 suppresses primary neurogenesis (Coffman et al., 1990; Coffman et al., 1993). These data suggest that the three territories of primary neurogenesis in Xenopus (medial, intermediate and lateral) are analogous to proneural clusters in Drosophila. This in turn implies the existence of one or more bHLH proteins whose expression defines these prospective neurogenic territories.

Several bHLH proteins expressed during Xenopus neurogenesis have been identified. One such protein, NeuroD, can exert a neuronal determination function when ectopically expressed, but the endogenous XNeuroD gene is not expressed early enough to play a proneural role (Lee et al., 1995). Several Xenopus homologs of achaete-scute have also been identified (Ferreiro et al., 1992; Zimmerman et al., 1993; Turner and Weintraub, 1994). Ectopic expression of one of these, XASH-3, can induce neural plate expansion (Ferreiro et al., 1994; Turner and Weintraub, 1994) or ectopic neurogenesis within the neural plate (Chitnis and Kintner, 1996), depending on the dose of injected RNA. Unlike NeuroD, however, XASH-3 is incapable of converting epidermal cells to neurons. Moreover, XASH-3 is expressed in a very restricted region of the neural plate, corresponding to the future sulcus limitans (Zimmerman et al., 1993). Thus, there must be other bHLH genes whose expression pattern and function are more consistent with proneural activity.

Accordingly, it is an object of the invention to provide such bHLH genes such as the neurogenin family. Thus, the invention provides recombinant neurogenin proteins and variants thereof, and to produce useful quantities of these neurogenin proteins using recombinant DNA techniques.

It is a further object of the invention to provide recombinant nucleic acids encoding neurogenin proteins, and expression vectors and host cells containing the nucleic acid encoding the neurogenin protein.

An additional object of the invention is to provide polyclonal and monoclonal antibodies directed against neurogenin proteins.

A further object of the invention is to provide methods for producing the neurogenin proteins.

SUMMARY OF THE INVENTION

In accordance with the objects outlined above, the present invention provides recombinant nucleic acids encoding neurogenin proteins.

In a further aspect, the invention provides expression vectors comprising transcriptional and translational regulatory DNA operably linked to DNA encoding a neurogenin protein, and host cells containing the expression vectors.

In an additional aspect, the invention provides methods for producing neurogenin proteins comprising the steps of culturing a host cell transformed with an expressing vector comprising a nucleic acid encoding a neurogenin protein and expressing the nucleic acid to produce a neurogenin protein.

In a further aspect, the invention provides recombinant neurogenin proteins.

In a further aspect, the invention provides polyclonal or monoclonal antibodies to neurogenin proteins.

BRIEF DESCRIPTION OF THE DRAWINGS

FIG. 1 depicts the alignment of the amino acid sequences of rat neurogenin-1 (top) (SEQ ID NO:1) and *Xenopus* (bottom; labelled X-NGNR-1.a) neurogenin-1 (SEQ ID NO:2). The bHLH region is marked in bold type. Solid lines indicated amino acid identity, the dots are conservative substitutions. Selection of the initiator methionine was according to Kozak's rule (Kozak, 1984), and identification of in-frame upstream termination codons (data not shown).

FIG. 2 depicts the alignment of the rat neurogenin-1 bHLH domain (SEQ ID NO:3) with other bHLH domains (SEQ ID NOS:4-11). Identity is shown in bold type. References for the compared sequences are: NeuroD (Lee et al., 1995)/BETA2 (Naya et al., 1995) (SEQ ID NO:5), MATH-2/Nex-1 (Bartholoma and Nave, 1994; Shimizu et al., 1995) (SEQ ID NO:6), MATH-1 (Akazawa et al., 1995) (SEQ ID NO:8), KW8 (Kume et al., 1996) (SEQ ID NO:7), *Drosophila* atonal (Jarman et al., 1993b) (SEQ ID NO:9), MASH1 (Johnson et al., 1990) (SEQ ID NO:10), AS-C T5 (Villares and Cabrera, 1987) (SEQ ID NO: 11).

FIG. 3 depicts the nucleic acid sequence of rat neurogenin 1 (SEQ ID. NO:12); the protein sequence is shown in SEQ ID NO:1.

FIG. 4 depicts the nucleic acid sequence of mouse neurogenin 1 (SEQ II). NO:13); the elucidated protein sequence is shown in SEQ ID NO:14.

FIG. 5 depicts the nucleic acid sequence of one of the *Xenopus* neurogenin 1 (SEQ ID NO:15) isoforms; the elucidated protein sequence is shown in SEQ ID NO:2.

FIG. 6 depicts the nucleic acid sequence of the other *Xenopus* neurogenin (SEQ ID NO:16) isoform; the protein sequence may be easily determined.

FIGS. 7A, 7B and 7C depict the nucleic acid sequence of mouse neurogenin 2 (SEQ ID. NO:17).

FIG. 8 depicts the amino acid sequence of mouse neurogenin 2 (SEQ ID NO:18). The bHLH domain is boxed.

FIGS. 9A and 9B depict the nucleic acid sequence of mouse neurogenin 3 (SEQ ID NO:19).

FIG. 10 depicts the amino acid sequence of mouse neurogenin 3 (SEQ ID NO:20). The bHLH domain is boxed.

FIG. 11 depicts the alignment of neurogenin 2 (SEQ ID NO:18) with *Xenopus* (bottom; labelled X-NGNR-1.a) (SEQ ID NO:2). The bHLH region is marked in bold type. Solid lines indicated amino acid identity, the dots are conservative substitutions. The two proteins exhibit 54% overall sequence identity and 68% overall sequence similarity to each other. Their bHLH domains (boxed) are 87% identical. Neurogenin 1 and neurogenin 3 exhibit similar extents of identity to X-NGNR-1.a within the bHLH domain, but exhibit 41 and 39% overall sequence identity with the *Xenopus* protein, respectively.

DETAILED DESCRIPTION OF THE INVENTION

The present invention provides novel neurogenin proteins. In a preferred embodiment, the neurogenin proteins are from vertebrates, more preferably from mammals, and in the preferred embodiment, from rats, mice or humans. However, using the techniques outlined below, neurogenin proteins from other organisms may also be obtained.

There are a number of closely related neurogenin proteins and nucleic acids that are all considered neurogenin proteins. As outlined below, there are at least three separate yet related neurogenin proteins in the mouse, neurogenin 1, neurogenin 2 and neurogenin 3. Neurogenin 1 has also been found in rat and *Xenopus*, and it is expected that at least all three neurogenin proteins are found in a number of organisms.

A neurogenin protein of the present invention may be identified in several ways. "Neurogenin" includes neurogenin 1, 2 or 3. A neurogenin nucleic acid or neurogenin protein is initially identified by substantial nucleic acid and/or amino acid sequence homology to the sequences shown in the Figures, including homology to neurogenin 1, 2 or 3. Such homology can be based upon the overall nucleic acid or amino acid sequence.

As used herein, a protein is a "neurogenin protein" if the overall homology of the protein sequence to the amino acid sequences of the neurogenins depicted herein is preferably greater than about 35% to 40%, more preferably greater than about 60% and most preferably greater than 80%. In some embodiments the homology will be as high as about 95 or 98%. This homology will be determined using standard techniques known in the art, such as the Best Fit sequence program described by Devereux et al., Nucl. Acid Res. 12:387-395 (1984) or the BLASTX program (Altschui et al., J. Mol. Biol. 215, 403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

Neurogenin proteins may be identified in one aspect by significant homology to the areas other than the bHLH domain, i.e. the N- and C-terminal portions of the sequences depicted in the Figures. This homology is preferably greater than about 40%, with greater than about 50 or 60% being particularly preferred and greater than about 80% being especially preferred. In some cases the homology will be greater than about 90 to 95 or 98%.

In addition, a neurogenin protein preferably also has significant homology to the neurogenin bHLH domain as described herein. This homology is preferably greater than about 75%, with greater than about 80% being particularly preferred and greater than about 85% being especially preferred. In some cases the homology will be greater than about 90 to 95 or 98%.

Neurogenin proteins of the present invention may be shorter or longer than the amino acid sequences shown in the Figures. Thus, in a preferred embodiment, included within the definition of neurogenin proteins are portions or fragments of the sequences depicted herein. Fragments of neurogenin proteins are considered neurogenin proteins if a) they share at least one antigenic epitope; b) have at least the indicated homology; c) and preferably have neurogenin biological activity.

Neurogenin proteins may also be identified as being encoded by neurogenin nucleic acids. Thus, neurogenin proteins are encoded by nucleic acids that will hybridize to the sequences depicted in FIGS. 3 (SEQ ID NO:12), 4 (SEQ ID NO:13), 5 (SEQ ID NO: 15), or 6 (SEQ ID NO: 16), as outlined herein.

In a preferred embodiment, when the neurogenin protein is to be used to generate antibodies, the neurogenin protein must share at least one epitope or determinant with one or more of the full length proteins depicted herein. By "epitope" or "determinant" herein is meant a portion of a protein which will generate and/or bind an antibody. Thus, in most instances, antibodies made to a smaller neurogenin protein will be able to bind to the full length protein. In a preferred embodiment, the epitope is unique; that is, antibodies generated to a unique epitope show little or no cross-reactivity, for example, with other bHLH domains. The neurogenin antibodies of the invention specifically bind to neurogenin proteins. By "specifically bind" herein is meant that the antibodies bind to the protein with a binding constant in the range of at least $10^4$-$10^6$ $M^{-1}$, with a preferred range being $10^4$-$10^9$ $M^{-1}$.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequences of FIGS. 3 (SEQ ID NO: 12), 4 (SEQ ID NO:13), 5 (SEQ ID NO:15), and 6 (SEQ ID NO:16) is preferably greater than 40%, more preferably greater than about 50%, particularly greater than about 60% and most preferably greater than 75%. In some embodiments the homology will be as high as about 80 to 90 to 95 or 98%.

In a preferred embodiment, a neurogenin nucleic acid encodes a neurogenin protein. As will be appreciated by those in the art, due to the degeneracy of the genetic code, an extremely large number of nucleic acids may be made, all of which encode the neurogenin proteins of the present invention. Thus, having identified a particular amino acid sequence, those skilled in the art could make any number of different nucleic acids, by simply modifying the sequence of one or more codons in a way which does not change the amino acid sequence of the neurogenin.

In one embodiment, the nucleic acid homology is determined through hybridization studies. Thus, for example, nucleic acids which hybridize under high stringency to the nucleic acid sequences shown in the Figures or their complements are considered neurogenin genes. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference.

In another embodiment, less stringent hybridization conditions are used; for example, moderate or low stringency conditions may be used, as are known in the art; see Maniatis and Ausubel, supra.

The neurogenin proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated neurogenin nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a neurogenin protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included with the definition of neurogenin protein are other neurogenin proteins of the neurogenin family, and neurogenin proteins from other organisms, which are cloned and expressed as outlined below. Thus, probe or degenerate polymerase chain reaction (PCR) primer sequences may be used to find other related neurogenin proteins from humans or other organisms. As will be appreciated by those in the art, particularly useful probe and/or PCR primer sequences include the unique areas of the neurogenin nucleic acid sequence. Thus, useful probe or primer sequences may be designed to the bHLH domain or the N- and C-terminal portions of the sequences. As shown in the examples, using the bHLH domain to generate probes can result in the cloning of both neurogenin proteins and related but distinct proteins, and thus if these sequences are used, further screening and/or sequencing may be required to identify neurogenin proteins. As is generally known in the art, preferred PCR primers are from about 15 to about 35 nucleotides in length, with from about 20 to about 30 being preferred, and may contain inosine as needed. The conditions for the PCR reaction are well known in the art.

Once the neurogenin nucleic acid is identified, it can be cloned and, if necessary, its constituent parts recombined to form the entire neurogenin protein nucleic acid. Once isolated from its natural source, e.g., contained within a plasmid or other vector or excised therefrom as a linear nucleic acid segment, the recombinant neurogenin nucleic acid can be further used as a probe to identify and isolate other neurogenin nucleic acids. It can also be used as a "precursor" nucleic acid to make modified or variant neurogenin nucleic acids and proteins.

Using the nucleic acids of the present invention which encode a neurogenin protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the neurogenin protein. "Operably linked" in this context means that the transcriptional and translational regulatory DNA is positioned relative to the coding sequence of the neurogenin protein in such a manner that transcription is initiated. Generally, this will mean that the promoter and transcriptional initiation or start sequences are positioned 5' to the neurogenin protein coding region. The transcriptional and translational regulatory nucleic acid will generally be appropriate to the host cell used to express the neurogenin protein; for example, transcriptional and translational regulatory nucleic acid sequences from *Bacillus* are preferably used to express the neurogenin protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells, Selection genes are well known in the art and will vary with the host cell used.

The neurogenin proteins of the present invention are produced by culturing a host cell transformed with an expression vector containing nucleic acid encoding a neurogenin protein, under the appropriate conditions to induce or cause expression of the neurogenin protein. The conditions appropriate for neurogenin protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melanogaster* cells, *Saccharomyces cerevisiae* and other yeasts, *E. coli*, *Bacillus subtilis*, SF9 cells, C129 cells, 293 cells, *Neurospora*, BHK, CHO, COS, and HeLa cells.

In a preferred embodiment, the neurogenin proteins are expressed in mammalian cells. Mammalian expression systems are also known in the art. A mammalian promoter is any DNA sequence capable of binding mammalian RNA polymerase and initiating the downstream (3') transcription of a coding sequence for neurogenin protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

The methods of introducing exogenous nucleic acid into mammalian hosts, as well as other hosts, is well known in the art, and will vary with the host cell used. Techniques include the use of viruses such as retroviruses and adenoviruses, dextran-mediated transfection, calcium phosphate precipitation, polybrene mediated transfection, protoplast fusion, electroporation, encapsulation of the polynucleotide(s) in liposomes, and direct microinjection of the DNA into nuclei.

In a preferred embodiment, neurogenin proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of neurogenin protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the neurogenin protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, neurogenin proteins are produced in insect cells. Expression vectors for the transformation of insect cells, and in particular, baculovirus-based expression vectors, are well known in the art.

In a preferred embodiment, neurogenin protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharormyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The neurogenin protein may also be made as a fusion protein, using techniques well known in the art. Thus, for example, for the creation of monoclonal antibodies, if the desired epitope is small, the neurogenin protein may be fused to a carrier protein to form an immunogen. Alternatively, the neurogenin protein may be made as a fusion protein to increase expression, or for other reasons.

Also included within the definition of neurogenin proteins of the present invention are amino acid sequence variants. These variants fall into one or more of three classes: substitutional, insertional or deletional variants. These variants ordinarily are prepared by site specific mutagenesis of nucleotides in the DNA encoding the neurogenin protein, using cassette or PCR mutagenesis or other techniques well known in the art, to produce DNA encoding the variant, and thereafter expressing the DNA in recombinant cell culture as outlined above. However, variant neurogenin protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the neurogenin protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed neurogenin variants screened for the optimal combination of desired activity. Techniques for making substitution mutations at predetermined sites in DNA having a known sequence are well known, for example, M13 primer mutagenesis and PCR mutagenesis. Screening of the mutants is done using assays of neurogenin protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. It should be noted that some of the neurogenin proteins differ substantially in length; thus, for example, mouse neurogenin 2 is 263 amino acids in length and mouse neurogenin 3 is 211 amino acids.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the neurogenin protein are desired, substitutions are generally made in accordance with the following chart:

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the neurogenin proteins as needed. Alternatively, the variant may be designed such that the biological activity of the neurogenin protein is altered.

In one embodiment, bHLH variants are made. In one embodiment, the bHLH domain may be eliminated entirely. Alternatively, any or all of the amino acids of a bHLH domain may be altered or deleted. In a preferred embodiment, one or more of the amino acids of the domain are substituted by other amino acids. Thus, amino acids corresponding to the neurogenin bHLH domain residues may be altered.

In one embodiment, the neurogenin nucleic acids, proteins and antibodies of the invention are labelled. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the neurogenin protein is purified or isolated after expression. Neurogenin proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the neurogenin protein may be purified using a standard anti-neurogenin antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the neurogenin protein. In some instances no purification will be necessary.

Once expressed and purified if necessary, the neurogenin proteins are useful in a number of applications as will be apparent to those in the art. For example, the proteins may be used to generate antibodies, which are then useful to purify the protein as outlined above. The antibodies are useful in diagnostic assays to detect neurogenin proteins. The proteins are also useful in neurogenesis.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Cloning of Rat and *Xenopus* Neurogenin 1 Genes

Previous work has identified MASH1 as a bHLH protein expressed in autonomic but not sensory ganglia of the mammalian PNS (Johnson et al., 1990; Lo et al., 1991; Guillemot and Joyner, 1993; Guillemot et al., 1993). We sought to isolate cDNAs encoding bHLH proteins expressed, conversely, in sensory but not autonomic ganglia. Degenerate RT-PCR was performed using cDNA prepared from embryonic day 13.5 (E13.5) rat dorsal root ganglia (DRG), using oligonucleotide primers derived from conserved regions of bHLH subfamilies including MASH1 and NeuroD). Random-primed cDNA template prepared from E13.5 rat embryonic DRGs was subjected to 40 cycles of PCR (1'@94° C.; 2'@45° C.; 2'@65° C.). The 5' primers were: 5'CGCGGATCC(A/C)GNAA(C/T)GA(A/G)(AC)G(G/C/T)GA(AG)(A/C)3' (SEQ ID NO:21) and 5'CGCGGATCCGCNAA(C/T)GC(A/C/T)(A/C)G(G/CT)GA(A/G)(A/C)G (SEQ ID NO:22), which were derived from RNERER (SEQ ID NO:29) and ANARER (SEQ ID NO:30), respectively, and contain a BamH1 site at the end. The 3' primers were 5'CCGGAATTCGT(T/C)TC(A/G/C)A(T/C)(T/C)TT(AG)CT(AC/G)A(A/G/T)(T/C)TT3' (SEQ ID NO:23) and 5'CCGGAATTCGT(T/C)TC(A/G/C)A(T/C)(T/C)TT(A/G/T)GA(A/C/G)A(A/G/T)(T/C)TT3' (SEQ ID NO:24), both of which are the reverse translation of K(L/M)SK(V/I)ET (SEQ ID NO:25) and contain a EcoRI site at the end. The 130 bp-PCR product was purified from a polyacrylamide gel, cloned into M13mp19 (New England Bio-labs), and sequenced. The ngn1 PCR product was then used to screen a lambda ZAP cDNA library prepared from rat E13.5 DRG (Saito et al., 1995). The isolated 1.2 kb and 1.7 kb cDNA clones were sequenced on both strands by Caltech sequencing core facility. The 1.7 kb cDNA fragment, encoding a predicted protein of 244 amino acid residues, was then used to screen a mouse lambda-2 129 genomic library (a gift of Z. Chen). From a 17-kb positive clone, a 2.0 kb fragment hybridizing to rat ngn1 cDNA was isolated and sequenced, which contains an open reading frame (ORF) differing from the rat one at six positions. The 2.2 kb-X-ngnr-1.a cDNA was isolated by screening a *Xenopus* St 17 cDNA library (Kintner and Melton, 1987) at low stringency using the rat cDNA as probe. An isoform of X-ngnr-1.a called X-ngnr-1.b was also isolated from this screen, and is depicted in the figures. X-ngnr-1.a and X-ngnr-1.b show the same expression patterns and phenotypes in mRNA injection (data not shown), and are referred to collectively as X-NGNR-1 in the text. Nucleotide sequences of the rat, mouse and two isoforms of the *Xenopus* neurogenin 1 have been deposited in GeneBank database.

Preliminary experiments indicated that mouse ngn1 mRNA caused ectopic neurogenesis when microinjected into *Xenopus* embryos (not shown), a phenotype similar to that obtained by over-expression of NeuroD (Lee et al., 1995). To determine whether this phenotype reflected the existence of a *Xenopus* gene with similar functional characteristics, the murine ngn1 cDNA probe was used to screen a stage 17 (St. 17) *Xenopus* cDNA library at low-stringency. Several ngn1-related cDNAs were obtained. This cDNA, which we have named *Xenopus* ngn-related-1 (X-ngnr-1), encodes a polypeptide of 215 amino acids displaying 82% sequence identity to mouse neurogenin within the bHLH domain (FIG. 2) (SEQ ID NO:4).

Example 2

Expression of Neurogenin 1 During Neurogenesis

Non-radioactive in situ hybridization to frozen sections of mouse embryos was performed as previously described (Birren et al., 1993). Whole-mount in situ hybridization was performed essentially as described (Chitnis et al., 1995) using digoxigenin-labelled antisense probes for X-NGNR-1, XNeuroD (Lee et al., 1995), X-Delta-1 and N-tubulin (Chitnis et al., 1995), with the following modification. At the step of developing the alkaline phosphatase reaction using NBT/BCIP substrates, 0.45 µl rather than 4.5 µl of NBT stock solution (75 mg/ml in 70% dimethyl formamide) was added to each 1 ml of staining buffer. This change reduced background staining and improved visualization of low-abundance mRNAs.

A preliminary analysis of ngn1 mRNA expression in mouse embryos by in situ hybridization revealed that expression of this gene is apparently restricted to the nervous system (data not shown). Within the nervous system, the expression of neurogenin 1 is spatially or lineally restricted; for example it is expressed in the ventral half of the spinal cord, except for a narrow domain just below the roofplate. In the peripheral nervous system, ngn1 mRNA is expressed in developing sensory but not in autonomic ganglia. Interestingly, a comparison of the expression of ngn1 and NeuroD expression on adjacent serial sections revealed that the two genes appear to be sequentially expressed in overlapping regions or neural cell populations. In the ventral spinal cord, for example, ngn1 mRNA is expressed throughout the ventricular zone, in regions where uncommitted progenitors are located, while NeuroD transcripts are expressed at the lateral border of the ventricular zone. However both genes show a similar dorsoventral restriction in their domains of expression within the spinal cord (except that NeuroD is not expressed below the roof plate). A similar spatial segregation is seen in the mesencephalic-diencephalic region. These data suggest that neurogenin 1 and NeuroD may function in similar regions of the murine nervous system but at sequential stages of neurogenesis.

A similar spatial overlap but temporal displacement was found for the expression of X-ngnr-1 and XNeuroD in Xenopus. For example, at St. 12, X-ngnr expression is observed in three broad patches within the neural plate, that demarcate the medial, intermediate and lateral territories where primary motorneurons, interneurons and sensory neurons, respectively, will later differentiate. In contrast, no XNeuroD expression is yet detected at this stage, nor have any primary neurons yet differentiated. XNeuroD mRNA can be detected at St. 13.5, in narrow rows of cells located within the three domains of primary neurogenesis which is already underway at this time. At this stage, X-ngnr-1 is expressed in a similar region of the neural plate but in many more cells than XNeuroD. A similar sequential expression of X-NGNR-1 and XNeuroD is seen in the trigeminal placode. Thus in Xenopus and in mouse, expression of neurogenin1/X-NGNR-1 precedes but spatially overlaps that of NeuroD/XNeuroD.

Example 3

Inducement of Neurogenesis

The observation that expression of X-ngnr-1 temporally and spatially prefigures the expression of XNeuroD, taken together with the sequence homology between the two genes, led us to test whether expression of X-NGNR-1 like that of XNeuroD is sufficient to induce premature and/or ectopic primary neurogenesis. We therefore injected X-ngnr-1 mRNA into one blastomere of two-cell stage embryos, and examined the pattern of neurogenesis after further development by whole mount in situ hybridization using a probe for N-tubulin, a neuron-specific marker in Xenopus (Chitnis et al., 1995). The distribution of β-galactosidase activity translated from a co-injected lacZ mRNA, as determined by counterstaining with XGal, was used to assess the overall distribution of the injected mRNAs in each individual embryo. Two types of negative controls were used: the uninjected side of the same embryo, and separate embryos injected only with lacZ mRNA.

The X-NGNR-1 open reading frame was cloned in-frame into the EcoR1 site of the vector pMT-CS2 (Turner and Weintraub, 1994). Capped X-NGNR-1 mRNA was transcribed using SP6 RNA polymerase as described (Kintner and Melton, 1987). X-NGNR-1 mRNA was co-injected with lacZ mRNA (as a marker) into one blastomeres of two-celled embryos (Coffman et al., 1993). Notch$^{ICD}$ and X-Delta-1$^{Stu}$ RNAs were prepared as described (Chitnis et al., 1995). Injection of LacZ mRNA alone was done as a control. Histochemical staining for β-galactosidase was performed to visualize the distribution of injected mRNAs. Embryos were collected at the neural plate stage (St13-14) or tail-bud stage (St 26) and subjected to in situ hybridization using probes as indicated in the figure legends. Animal cap assays were performed as described previously (Ferreiro et al., 1994).

Over-expression of X-ngnr-1 mRNA caused extensive ectopic neurogenesis within the neural plate (100% of embryos examined; ≥100 embryos injected).

At St. 13.5, for example, nearly every cell on the injected side of the embryo appeared to express N-tubulin, whereas on the uninjected side the three stripes of primary neurogenesis were clearly distinguishable (data not shown); moreover within these stripes the distribution of neurons was more scattered than on the injected side. In addition to the increased extent of neurogenesis, the timing of neuronal differentiation was accelerated on the injected side, so that N-tubulin cells were seen on the injected side at St. 12.5, a time at which no expression of this marker was detected on the contralateral control side (not shown). Moreover, X-ngnr-1 also caused ectopic neuronal differentiation in regions of non-neurogenic ectoderm that flank the neural plate. The consequence of this was most easily observed at St. 24-26 (tail bud stage), where supernumerary neurons were observed within the epidermis. Extensive ectopic neurogenesis was also observed in the most anterior part of the embryo, where for example the eye was missing and replaced by amorphous neural tissue (data not shown). In these respects, the phenotype of X-ngnr-1 mRNA-injected embryos appeared similar or identical to that previously reported for XNeuroD (Lee et al., 1995). In the latter case, it has been confirmed by injections at the 32-cell stage that the ectopic neurons in the skin indeed reflect a conversion of non-neurogenic ectoderm (and not, for example, simply conversion of migrating trunk neural crest cells) (Lee et al., 1995), and we infer by extension that the same holds true for X-NGNR-1-injected embryos.

The fact that over-expression of X-ngnr-1 yielded an XNeuroD-like phenotype, coupled with the fact that endogenous X-ngnr-1 expression temporally precedes and overlaps that of XNeuroD, suggested that the latter might be a target of transcriptional activation by the former. To test this, embryos injected with X-ngnr-1 mRNA were hybridized with an XNeuroD probe. A massive, ectopic induction of endogenous XNeuroD mRNA was observed in X-ngnr-1 mRNA-injected embryos (100% of embryos examined; >50 embryos injected). The extent of ectopic expression was similar to that observed with an N-tubulin probe. By contrast, injection of XNeuroD mRNA did not increase the expression of endogenous X-ngnr-1 mRNA, although it did induce ectopic neurogenesis as previously reported (Lee et al., 1995). These data suggest that the neurogenic phenotype of X-ngnr-1 mRNA-injected embryos may reflect an induction of endogenous XNeuroD, and suggest that the sequential expression of these two genes during *Xenopus* neurogenesis reflects a unidirectional cascade in which the former induces transcription of the latter.

To ensure that the ectopic neurogenesis promoted by injection of X-NGNR-1 RNA was not a secondary consequence of induction of mesodermal tissue, we performed animal cap experiments. Animal caps from embryos injected in both blastomeres with various RNAs at the 2-cell stage were dissected and allowed to develop in vitro, after which time they were assayed for expression of various marker mRNAs by RNase protection (Ferreiro et al., 1994). As expected from the whole mount in situ analysis, injection of X-NGNR-1 RNA caused induction of expression of N-tubulin mRNA. No mesodermal induction was detected under these conditions, by criteria of expression of muscle-specific actin mRNA (Ferreiro et al., 1994). This control experiment indicates that the promotion of neurogenesis by X-NGNR-1 is a direct effect on naive ectoderm, and not an indirect result of mesoderm induction.

The effect of X-NGNR-1 was also compared to that of noggin (Smith and Harland, 1992) in the animal cap experiments. Noggin, which promotes neural induction (Lamb et al., 1993) by antagonizing the epidermalizing effect of BMP-4 (Sasai et al., 1995), induced expression of NCAM, a marker of undifferentiated neural tissue (Kintner and Melton, 1987), but not of the neuronal differentiation marker N-tubulin (Chitnis et al., 1995). X-NGNR-1, by contrast, induced expression of both NCAM and N-tubulin mRNAs, although the level of the latter transcript was higher. These data are consistent with the idea that noggin promotes neuralization but is insufficient for neuronal differentiation (Ferreiro et al., 1994), while X-NGNR-1 promotes both neuralization and consequent neuronal differentiation.

X-NGNR-1 Expression Precedes, and can Activate Expression of, X-Delta-1

The foregoing data indicated that X-ngnr-1 is expressed earlier than XNeuroD, and is capable of inducing expression of XNeuroD as well as of promoting ectopic neurogenesis. Thus, like NeuroD, X-NGNR-1 can exert a neuronal determination function when over-expressed. But can X-NGNR-1 normally play this role in vivo? To address this question we examined the timing of X-NGNR-1 expression relative to that of X-Delta-1. In *Xenopus* as in *Drosophila*, X-Delta-1 encodes a lateral inhibitory ligand that controls a choice between neuronal and non-neuronal fates (Chitnis et al., 1995). By definition, therefore, at the time Delta is first expressed this choice has not yet been made.

During early gastrulation (St. 10.5), X-ngnr-1 mRNA can be detected at the lateral margins of the prospective neural plate. At this stage, X-Delta-1 mRNA is not yet expressed in this region, although it is detected in an area adjacent to the blastopore. By midgastrulation (St. 11.5), both X-ngnr-1 and X-Delta-1 mRNAs can be detected in three distinct patches within the neural plate, prefiguring the regions where primary neurogenesis will occur. Within these regions the domain of X-ngnr-1 expression appears to encompass that of X-Delta-1. At the same stage, X-ngnr-1 expression can be observed in the presumptive trigeminal placode, where X-Delta-1 mRNA is not yet detectable. At neither of these stages is expression of XNeuroD detected (not shown). These data indicate that expression of X-ngnr-1 precedes that of X-Delta-1 in both the CNS (neural plate) and the PNS (trigeminal placode), whereas XNeuroD is not expressed until after X-Delta-1.

In *Drosophila*, the proneural genes (achaete-scute) activate expression of Delta (Hinz et al., 1994; Kunisch et al., 1994). The fact that expression of X-ngnr-1 precedes but spatially overlaps that of X-Delta-1 suggested, therefore, that the former might be capable of activating expression of the latter. In support of this idea, injection of synthetic X-NGNR-1 RNA induced ectopic expression of endogenous X-Delta-1 mRNA (100% of embryos examined; ≥50 embryos injected), whereas control injections of lacZ mRNA had no such effect. Thus, like the proneural genes in *Drosophila*, X-ngnr-1 can activate expression of a lateral inhibitory ligand that controls a choice between neuronal and non-neuronal fates, within a group of developmentally equivalent cells.

Xnotch1$^{ICD}$ Inhibits Both the Expression and Function of X-NGNR-1

Within the three domains of the neural plate, X-ngnr-1 mRNA-expressing cells appear scattered, rather than contiguous. In *Drosophila*, the expression of achaete-scute is restricted to sensory organ precursor cells by lateral inhibitory interactions mediated by Notch and Delta (Ghysen et al., 1993). This suggested by analogy that the expression of X-ngnr-1 might similarly be restricted to subsets of neural precursors by lateral inhibition. Three different experiments support this idea. First, injection of a dominant-active form of Notch (Struhl et al., 1993) (the intracellular domain, or ICD), which inhibits primary neurogenesis, also repressed the expression of endogenous X-ngnr-1 mRNA (18/18 embryos tested); in contrast control injections of lacZ mRNA had no such effect. Conversely, blocking lateral inhibition by injection of a dominant-negative form of X-Delta-1 (X-Delta-1$^{Stu}$) (Chitnis et al., 1995), caused an apparent increase in the density of strongly X-ngnr-1-positive cells, as well as a slight expansion of the X-ngnr-1-positive domain in 60% of injected embryos (31/50 embryos tested). In contrast such an effect was not seen in control lacZ-injected embryos (except in one isolated case out of 39 embryos examined). This second result suggested that the density of X-ngnr-1-expressing cells within each domain of primary neurogenesis is normally limited by lateral inhibition. The fact that exogenous Notch$^{ICD}$ is, moreover, able to strongly suppress endogenous X-ngnr-1 expression supports the idea that this lateral inhibition is mediated, at least in part, by endogenous X-Notch genes.

To determine whether Notch-mediated signalling can inhibit the function as well as the expression of X-ngnr-1, exogenous X-ngnr-1 mRNA was co-injected with either lacZ mRNA, or lacZ mRNA plus Notch$^{ICD}$ mRNA. An inhibition of X-ngnr-1-promoted ectopic neurogenesis was observed with high penetrance (27/29 embryos tested), indicating that the function as well as the expression of X-NGNR-1 is sensitive to inhibition by Notch$^{ICD}$. However, within the injected side of the experimental embryos, the inhibition of neurogenesis showed variable expressivity, and appeared most complete in those regions which received the highest amount of the co-injected mRNAs (as determined by XGal staining). Assuming that all three co-injected mRNAs are similarly distributed, this result could indicate that a certain threshold amount of Notch$^{ICD}$ mRNA is necessary to overcome neurogenesis promoted by exogenous X-ngnr-1 mRNA, and/or that there is a non-linear relationship between the amount of Notch$^{ICD}$ mRNA injected and the amount of inhibitory activity produced.

The initial expression of X-ngnr-1 occurs in three territories (medial, intermediate and lateral) which demarcate the domains in which primary neurogenesis will eventually occur (Chitnis et al., 1995). Our data suggest that within these territories, lateral inhibition restricts X-NGNR-1 expression to a limited number of neuronal precursor cells. During this process, X-NGNR-1 positively regulates X-Delta-1, and is in turn negatively regulated (in adjacent cells) by signalling through X-Notch-1, a receptor for X-Delta-1. Thus cells expressing higher levels of X-NGNR-1 will inhibit expression of X-NGNR-1 in their neighbors and thereby suffer less inhibition, leading to yet higher levels of X-NGNR-1 expression, and so on. As X-NGNR-1 expression becomes restricted to presumptive neuronal precursors, it leads (directly or indirectly) to expression of XNeuroD. Once the cells express sufficiently high levels of XNeuroD, they undergo neuronal differentiation. In this view, lateral inhibition is part-and-parcel of the cell fate decision process itself, although it may also be engaged to prevent further differentiation after the decision has been made.

This model postulates a role for X-NGNR-1 that is analogous to that deduced for the *Drosophila* proneural genes, such as achaete-scute and atonal, from both loss-of-function and gain-of-function genetic experiments (Ghysen et al., 1993). While *Xenopus* is advantageous for gain-of-function perturbations, loss-of-function perturbations are less readily achieved in this system. However our conclusions are not based solely on gain-of-function phenotypes, but also on the timing and place of X-ngnr-1 expression in relation to that of other regulatory genes, as well as on the regulation of endogenous X-ngnr-1 mRNA expression by manipulation of the lateral inhibition machinery.

For example, our conclusion that X-Delta-1 is positively regulated by X-NGNR-1 is consistent with the fact that the initial expression of X-ngnr-1 precedes and spatially overlaps that of X-Delta-1, as well as with the fact that injection of X-ngnr-1 mRNA induces ectopic expression of endogenous X-Delta-1 mRNA. Similarly, in *Drosophila*, the proneural genes positively regulate expression of Delta (Hinz et al., 1994; Kunisch et al., 1994). Likewise, our conclusion that expression of X-ngnr-1 is restricted to subsets of cells by lateral inhibition is consistent with the observation that this gene exhibits a scattered pattern of expression within each of the three territories of primary neurogenesis, and that the density of X-NGNR-1-expressing cells can be increased within these territories by injection of a dominant-negative form of X-Delta-1. Finally, there is a good correlation between the ability of injected X-Delta-1$^{Stu}$ mRNA to increase the density of X-NGNR-1 expressing cells, and also to increase the density of N-tubulin-expressing cells which subsequently differentiate. This correlation suggests that the number of neuronal precursors may normally be determined by the number of cells that express X-NGNR-1 above a given threshold level.

The observation that X-ngnr-1 both activates, and is inhibited by, the lateral inhibitory circuitry raises the paradox of how a neurogenic phenotype can nevertheless be obtained by over-expressing this gene. The simplest answer is that the injected X-NGNR-1 RNA bypasses X-Notch-mediated transcriptional repression of the endogenous X-ngnr-1 gene. However, our data suggest that Notch is also able inhibit the function of X-NGNR-1 translated from exogenous RNA, either by a post-transcriptional mechanism or by inhibiting expression of X-NGNR-1 target genes. Nevertheless, this inhibition appears to require high levels of X-Notch$^{ICD}$ expression, being strongest in those regions which contain the highest level of co-injected RNAs.

In the situation where X-NGNR-1 RNA alone is injected, the level of endogenous X-Notch signalling may simply be insufficient to override the large amounts of exogenous X-NGNR-1 protein. Moreover, the possibility that Notch$^{ICD}$ inhibits X-NGNR-1 function artefactually, because it is injected in a form that normally does not exist in vivo (see (Nye et al., 1994) for further discussion), cannot be excluded.

Relationship of XASH-3 and X-NGNR-1

Xash3 is the only other neural bHLH gene which is known to be expressed as early as X-ngr-1 in the neural plate (Zimmerman et al., 1993). The available evidence, however, more clearly identifies X-ngnr-1 as a vertebrate analog of the *Drosophila* proneural genes during primary neurogenesis. Firstly, while the expression of X-ngnr-1 correlates extremely well with the three domains of the neural plate where primary neurons form, Xash-3 is expressed in an "intermediate" zone of the neural plate which may in fact correspond to the sulcus limitans (Zimmerman et al., 1993). Secondly, the activity of Xash3 in ectopic expression studies appears to be different from that of X-NGNR-1. For instance, ectopic expression of XASH-3 at high levels causes an expansion of neural tissue (Ferreiro et al., 1994; Turner and Weintraub, 1994), a phenotype never observed with X-NGNR-1. Ectopic expression of XASH-3 can also induce ectopic neuronal differentiation, but only effectively when lateral inhibition is also blocked using the dominant-negative X-Delta-1, and only then within the posterior neural plate (Chitnis and Kintner, 1996). X-NGNR-1 does not have similar restrictions in its activity, and can promote neurogenesis anteriorly, and outside the neural plate. Finally, although exogenous XASH-3 is sensitive to lateral inhibition mediated by X-Notch-1 and X-Delta-1 (Chitnis and Kintner, 1996), there is no evidence that endogenous Xash-3 expression is normally regulated by such inhibition. Thus, X-ngnr-1 fulfills more of the criteria expected for a gene whose activity defines the "proneural" domains wherein primary neurons arise in the neural plate.

The function of Xash-3 remains enigmatic. The fact that ectopic expression of this gene expands undifferentiated neural tissue suggests that it could normally act to prevent or delay overt neuronal differentiation within the restricted domain of the neural plate where it is expressed. Consistent with this idea, injection of Notch$^{ICD}$ which expands the neural plate also expands the domain of Xash-3 mRNA expression (unpublished observations). This is exactly the opposite of what is observed in the case of X-ngnr-1, whose expression is repressed under these conditions. An insensitivity of Xash-3 to transcriptional inhibition by X-Notch-1 signalling would allow the continued expression of this gene to maintain the uncommitted neural character of neural plate cells, while the high sensitivity of XASH-3 to functional inhibition by Notch (Chitnis and Kintner, 1996) would prevent these cells from undergoing overt neuronal differentiation. Whether XASH-3 also contributes to primary or secondary neurogenesis, but in different cells or at a different step in the pathway as X-NGNR-1, remains to be determined.

X-NGNR-1 Performs Two Distinct and Temporally Separated Functions

In our experiments, injection of X-ngnr-1 mRNA results in the induction of both X-Delta-1 and XNeuroD. During normal development, however, expression of XNeuroD is delayed relative to that of X-Delta-1. How is the sequential expression of these two putative target genes of X-NGNR-1 normally achieved? One possibility is that X-Delta-1 requires a lower threshold of X-NGNR-1 activity than XNeuroD to be activated, and that it takes time for X-NGNR-1 to accumulate to levels sufficient to induce XNeuroD. Another explanation is that a co-factor is required together with X-NGNR-1 to activate XNeuroD, and that expression of this co-factor is delayed. Precedent for such a temporal separation of transcription factor functions is found during mother-daughter segregation in yeast, where the Swi5 protein acts first to activate ASH1 expression (which in turn blocks Swi5p function in daughter cells (Bobola et al., 1996; Sil and Herskowitz, 1996)), and later to activate HO expression in mother cells. The delay in HO activation by Swi5p reflects an induction of the necessary co-activators Swi4p and Swi6p (Amon, 1996). Interestingly, in both *Xenopus* neurogenesis and yeast the temporal separation provides a time window for these determinative factors (Swi5p or X-NGNR-1) to provide an inhibitory signal to neighboring or daughter cells, while allowing them to later promote an alternative fate cell-autonomously.

Determination Versus Differentiation Genes

We have documented a sequential expression of ngn1 and NeuroD mRNAs during both murine and *Xenopus* neurogenesis, and in the latter system have further demonstrated a unidirectional functional cascade for these genes. Thus in *Xenopus* neurogenesis, as in mammalian skeletal myogenesis and *Drosophila* neurogenesis, structurally-related bHLH proteins function in cascades (Jan and Jan, 1993). The timing and location of NeuroD expression have previously been suggested to reflect a function for this gene in neuronal differentiation (Lee et al., 1995), perhaps analogous to that of myogenin during muscle development (for review, see (Weintraub, 1993)). By extension, the upstream gene X-ngnr-1 would function in determination, analogous to the roles of MyoD and myf5 during myogenesis. Such a conclusion would be consistent with our demonstration that the regulation and function of X-ngnr-1 are similar to that of the proneural genes, which control the determination of neural precursors in *Drosophila* (Campuzano and Modolell, 1992).

What is different about determination and differentiation bHLH factors? The similar actions of these proteins in gain-of-function experiments suggest that they may differ only in the time and place of their expression, or in the downstream genes they regulate (Jan and Jan, 1993). On the other hand, they may possess intrinsic functional differences that have so far escaped detection. For example, it has been proposed that muscle differentiation factors are less sensitive to inhibitors than are determination factors (Weintraub, 1993). However, such a differential sensitivity to inhibitors has not been demonstrated in myogenesis, although MyoD function can be inhibited by Notch$^{ICD}$ (Kopan et al., 1994).

Previously, a differential sensitivity of XASH-3 and XNeuroD to lateral inhibition was demonstrated (Chitnis and Kintner, 1996). Although Xash-3 is expressed earlier than XNeuroD, there is no evidence that the two genes function in a cascade; indeed the latter gene is expressed in many regions where it is not preceded by the former. While X-NGNR-1 and XNeuroD do appear to function in a cascade, they do not appear differentially sensitive to inhibition by co-injected X-Notch$^{ICD}$, in side-by-side comparisons (Ma et al., unpublished data). It is possible that these genes are differentially sensitive to direct inhibition by Notch signalling at the transcriptional level, but this is currently difficult to test since inhibition of X-NGNR-1 expression by Notch$^{ICD}$ indirectly prevents expression of XNeuroD.

The determination function proposed for X-ngnr-1 may, therefore, primarily reflect the developmental context in which this gene is expressed. Expression of X-ngnr-1 in the neurectoderm generates a group of competent cells, from which a subset is later selected for overt neuronal differentiation. The state of competence imposed by X-ngnr-1 expression is insufficient to allow differentiation, precisely because the expression and function of this gene are sensitive to lateral inhibition. However, through its ability to upregulate X-Delta-1, X-NGNR-1 confers the capacity to engage in a winner-take-all competition between alternative cell states: neuronal or non-neuronal. While increased expression of X-NGNR-1 imposes a bias towards the neuronal state, this state is unstable until subsequent events render the cell insensitive to further inhibition. The nature of the events that stabilize the neuronal state and commit the cell irreversibly to neuronal differentiation remain to be established.

Example 4

Cloning of Neurogenin 2 and Neurogenin 3 from Mouse

In an extension of the above approach, additional genes were cloned, using Monc-1 cells, an immortalized neural crest cell line which can be grown under differentiated or undifferentiated conditions (Sommer, et al., (1995). Neuron. 15, 1245-1258.).

RT-PCR and Isolation of bHLH Transcription Factor cDNA Clones

Total cellular RNA was extracted (Chomczynski and Sacchi, (1987) Anal. Biochem. 162, 156-159) from Monc-1 cells (Sommer et al., 1995) that had been differentiated for two days. Oligo-dT primed reverse transcription of total RNA was carried out for 1 hr at 42° C. using Superscript II (Gibco). First strand cDNA served as template for PCR amplification using Taq polymerase (Fisher) and the following degenerate primers: Asc10 (5' primer; cgggatccAAT/C GA/CI C/AGI GAA/G C/AGI AAT/C C/AGI A/GT) (SEQ ID NO:26); and Asc11 (3'primer; cggaattcAG/AI GTT/C TCI AT/CT/C TTI G/CA/TI AT/G/AT/C TT) (SEQ ID NO:27). The Asc10 primer encodes NE/ARERNRV/M (SEQ ID NO:28) and contains a BamHI site (small letters) at the 5' end. The Asc11 primer encodes the reverse translation of KM/LSKV/IETL (SEQ ID NO:31) and includes an EcoRI site (small letters) at the 5' end.

PCR was carried out in a Perkin Elmer DNA Thermal Cycler for 8 cycles with a denaturation step at 94° C. for 1 min, annealing at 43° C. for 1 min and extension at 72° C. for 1 min, followed by an additional 40 cycles with the annealing temperature raised to 55° C. The Taq polymerase was added at 94° C. during the first cycle using Amplivax (Perkin Elmer). The 130 bp PCR product was purified from a NuSieve agarose gel (FMC Bioproducts) by Qiaquick (Qiagen), subject to a second round of PCR (40 cycles of 1' at 90° C., 1' at 55° C., 1' at 72° C.), digested with EcoRI and BamHI, and cloned into the Bluescript SK-vector (pBS) (Stratagene Cloning Systems). Altogether, 70 clones were characterized, and identified according to the sequences of helix 1 and the loop.

They comprised MASH1 (Johnson, et al., (1990) Nature. 346, 858-861) (8 clones), SCLERAXIS (Cserjesi et al., (1995) Development 121, 1099-1110) (5 clones), as well as the eight ATONAL-related factors. Among those, NGN1 was represented by 14 clones; NGN2, 4 clones; NGN3, 16 clones; NeuroD, 1 clone; MATH2/Nex1, 2 clones; NDRF/KW8/NeuroD2, 2 clones; NeuroD4, 5 clones; and NeuroD5, 1 clone; the sequences of the rest of the 70 clones did not represent bHLH factors.

Isolation of ngn2 and ngn3 Genomic Clones

The PCR products encoding the novel bHLH domains were used individually to screen a mouse lambda-2 129 genomic library (a gift from Z. Chen). From positive genomic clones containing the genes ngn2 and ngn3, respectively, a 2.0 kb (ngn2) and a 1.8 kb (ngn3) restriction fragment hybridizing to the respective PCR products were isolated, cloned into pBS, and then sequenced on both strands by the Caltech sequencing core facility.

The PCR fragments encoding the helix 1-loop domain of ngn2 and ngn3 were then used individually as hybridization probes to isolate clones containing additional coding sequences from a mouse genomic library. Hybridizing restriction fragments from these genomic clones were subcloned and sequenced. Sequencing of these subclones revealed that the open reading frames of both ngn2 and ngn3 are each contained within a single exon, a situation similar to that of other bHLH genes previously characterized, such as Mash1 (Guillemot et al., 1993). The deduced polypeptide sequences of NGN2 and NGN3 consist of 263 and 214 amino acids, respectively (FIG. 1A), and display a 41-47% overall sequence identity to each other and to NGN1. Of the three members of the NEUROGENIN-subfamily known so far in mouse, NGN2 shows the highest homology to *Xenopus* NGN-RELATED FACTOR-1a (X-NGNR-1a), a protein suggested to control the choice of neuronal fate by uncommitted neural plate cells in *Xenopus* (Ma et al., 1996). (54% overall sequence identity of NGN2 to X-NGNR-1a, vs. 41% for NGN1 and 39% for NGN3; see FIG. 1 (SEQ ID NOS:1 and 2) and (Ma et al., 1996)).

Alignment of the bHLH domains of NGN2 and NGN3 with those of other murine ATONAL-like sequences identified in this study revealed that these bHLH domains define two distinct subfamilies. The first subfamily consists of NGN1, NGN2 and NGN3, while the members of the second subfamily are very similar to NeuroD (Lee et al., 1995; Naya et al., 1995) and comprise MATH2/Nex1 (Bartholoma and Nave, 1994; Shimizu et al., 1995) and NDRF/KW8/NeuroD2 (Kume et al., 1996; McCormick et al., 1996; Yasunami et al., 1996). In the NEUROGENIN subfamily, the junction region between the basic domain and helix 1 ("jnc.") as well as many residues of the loop and helix 2 are highly conserved. Within this region, moreover, several amino acids are conserved among all members of the NEUROGENIN subfamily but are divergent in members of the NeuroD subfamily.

Members of the NeuroD subfamily, on the other hand, are characterized by sequence identity within the loop region and helix 2 (in contrast to the NEUROGENIN subfamily members). Furthermore the sequence of the loop is specific for members of the NeuroD subfamily, as are several amino acids in helix 2 (FIG. 2, dotted residues in NeuroD consensus). On this basis, we have tentatively assigned to this subfamily two additional novel ATONAL-like sequences isolated in our screen, called NeuroD4 and NeuroD5. Confirmation of this assignment will await the isolation of full-length clones for these two genes. The sequence of MATH 1, the first mammalian ATONAL homolog to be isolated (Akazawa et al., 1995), was not detected in our RT-PCR screen. It was not included in the comparison presented here because it does not fit well in either subfamily, and may represent yet a third subfamily of ATONAL-like genes.

In Situ Hybridization

Non-radioactive in situ hybridization with digoxigenin labeled riboprobes was carried out on frozen sections of paraformaldehyde-fixed mouse embryos according to Birren et al. (Birren et al., (1993) Development 119, 597-610). Non-radioactive whole mount in situ hybridization was performed using a modification of the procedure described by Wilkinson (Wilkinson, (1992) In Situ Hybridization: A Practical Approach, ed. D. G. Wilkinson, IRL Press, Oxford). Antisense riboprobes used were as follows: ngn2 and ngn3 (isolated in this study); ngn1 (Ma et al., (1996) Cell 87, in press); neuroD (Lee, et al., (1995). Science. 268, 836-844.); and rat erbB3 (a gift from Hal Wang).

ngn2 Expression Precedes that of ngn1 in Both the Spinal Cord and the Neural Crest The expression of the ngn's in the trunk region was investigated, by performing in situ hybridization to transverse sections of developing mouse embryos. Between E8.5 and E10.5, both ngn1 and ngn2 become strongly expressed in the ventricular zone (VZ) of the ventral neural tube, as well as in a limited area of the dorsal neural tube near the roof plate. In the dorsal neural tube, however, the domain of ngn2 expression was broader than that of ngn1. This difference was also observed at E12, when ngn1 expression became restricted to the basal half of the neural tube and a narrow stripe adjacent to the roof plate, while ngn2 expression persisted throughout the dorso-ventral axis of the spinal cord (data not shown; see also Ma et al., 1996). Interestingly, ngn1 was expressed in a more lateral part of the VZ while ngn2 was detectable in both the medial and lateral parts of the VZ. In contrast to ngn1 and ngn2, ngn3 mRNA was most strongly expressed in a very restricted region of the spinal cord, just dorsal to the floor plate, which was detectable as early as E9 and persisted until E14 (data not shown) when a few ngn3-expressing cells were still detectable in this region. At E12, however, a second more dorsally-located domain of weaker ngn3 expression was detected. This second domain appeared to overlap with the expression of both ngn1 and ngn2, however ngn3 was expressed closer to the ependymal canal than was ngn1, in this region.

In the peripheral nervous system (PNS), ngn2 expression clearly preceded that of ngn1 and was detectable in cells dorso-lateral to the neural tube as early as E8.5. On adjacent sections, ngn1 mRNA was not yet detectable in this region. The timing and location of ngn2 expression in this position strongly suggests that this gene is expressed by migrating neural crest cells, a conclusion supported by whole mount in situ hybridization experiments, At E10.5, persistent but weak ngn2 expression was detected in subsets of cells in the trunk dorsal root sensory ganglia (DRG), which also contained more numerous ngn1-expressing cells as previously shown (Ma et al., 1996). The position and morphology of the ngn2-expressing cells, which are located at the dorso-lateral aspect of the DRG, suggests that they are non-neuronal cells, either neuronal precursors and/or satellite cells. Neither ngn2 nor ngn1 were detectable in sympathetic or enteric ganglia (not shown), which instead express the bHLH factor Mash1 (Lo, et al., (1991). Genes & Dev. 5, 1524-1537). ngn2 expression in DRG was rapidly extinguished, so that by E12 no signal was detectable. In contrast, ngn1 expression in trunk DRG persisted through E12 and was not extinguished until E14 (data not shown). Expression of ngn3 was not detected in either trunk neural crest or its derivatives at any of the stages examined.

Apparent Axial Differences in Neural Crest and its Derivatives Defined by ngn2 Expression To obtain further evidence that ngn2 is expressed by early-migrating trunk neural crest cells, the expression of this gene was examined at E8.5-E9.5 by whole mount in situ hybridization. At E9.25, ngn2 was expressed in two longitudinal stripes, that define its dorsal and ventral domains of expression in the spinal cord. A third longitudinal stripe of ngn2 expression was also detected ventro-lateral to the dorsal stripe. The position of this stripe was consistent with the idea that it represents expression of ngn2 in early emigrating crest cells. This interpretation is supported by the similar location of cells expressing erbB3, an independent marker of migrating neural crest (Meyer and Birchmeier, (1995) Nature 378, 386-390). Surprisingly, the domain of strong ngn2-expression in neural crest seemed not to extend as far anteriorly as did the domains of its expression in the spinal cord, but rather declined sharply within the cervical region. Analysis of embryos from earlier stages confirmed that ngn2 expression in neural crest of cervical regions was low or undetectable at E8.5 as well (data not shown). In contrast migrating crest cells expressing erbB3 were detectable in the cervical region as well as in the trunk. However, we cannot presently distinguish whether the relatively lower level of ngn2 expression in cranial crest reflects a true difference in its expression by neural crest cells, or rather fewer crest cells in this region at the stages we examined.

Nevertheless, an apparent axial difference in levels of ngn2 expression by neural crest cells was supported by the analysis of transverse sections through the thoracolumbar and cervical regions of E8.5 embryos. Moreover, similar axial differences were observed in forming DRG at later developmental stages. This prediction was confirmed by comparison of transverse sections through different axial levels of later stage embryos. At both E9.5 and E10.5, ngn2 transcripts were detectable in DRG at thoracolumbar but not cervical regions. By contrast, ganglia at both axial levels express ngn1 mRNA as detected on adjacent serial sections. Taken together, these data suggest that cells expressing ngn2 contribute mainly to developing DRGs of the thoracolumbar but not the cervical level. This in turn provides molecular evidence that trunk neural crest might be distinct from cervical neural crest from the earliest stages of migration.

In contrast to the low or undetectable levels of ngn2 expression in migrating cervical neural crest cells, the transcript was abundantly expressed in the epibranchial placodes. This difference appears to correlate with the fact that these placodes contribute neurons to most of the cranial sensory ganglia, while the non-neuronal cells derive from the neural crest in this region (for review, see (Noden, (1993) J. Neurobiol. 24, 248-261). Consistent with this correlation, ngn2 mRNA was later detected in several (but not all) of the cranial sensory ganglia, including the VII$^{th}$ and IX$^{th}$ ganglia (see below). This correlation supports, but does not prove, the idea that many of the ngn2 expressing cells are precursors to neurons, an idea consistent with the function of the ngn2 homolog X-ngnr-1 in *Xenopus* neurogenesis (Ma, et al., 1996).

Neurogenins Exhibit Partially-Overlapping Domains of Expression in the Developing CNS Previous studies of ngn1 (Ma et al., 1996) as well as our whole mount in situ hybridization data indicated that members of the ngn subfamily are also expressed in the developing brain. To further characterize this expression we hybridized adjacent transverse sections through E12 embryos with probes for the three ngn's. Both ngn1 and ngn2 were expressed in common but restricted regions of the CNS, in the VZ, For example, high levels of ngn2 mRNA were detected in cortical neuroepithelium, which also expressed ngn1 albeit at much lower levels. Similarly, a portion of the diencephalon expressed high levels of ngn2 and lower levels of ngn1. Interestingly, the expression domains of the ngn's collectively excluded large areas, such as the striatum, which instead express Mash (Lo et al., (1991) Genes & Dev. 5, 1524-1537). In other studies we have shown by double-label in situ hybridization that the domains of ngn1 and Mash1 expression in the developing forebrain are complementary and non-overlapping (Ma et al., in preparation). Thus the expression domains of the ngn's and Mash1 appear collectively to account for most or all of the neuroepithelium of the CNS and the ganglia of the PNS.

Although at first sight, the domains of ngn1 and ngn2 expression in the developing brain appeared co-extensive, closer inspection revealed that in some areas the boundaries of ngn2 expression were distinct from those of ngn1. For instance, at E10.5 the ventral boundary of ngn2 mRNA expression in developing cortex appeared to extend slightly below that of ngn1 (data not shown). Similarly, in sagittal sections of E12 hindbrain, the domain of ngn2 expression extended posterior to that of ngn1. Such cases of partial overlap were observed in other areas of the brain as well. For example at E12 in parasagittal sections through the lateral part of the dorsal thalamus, ngn2 but not ngn1 was detected, while both transcripts were detected in mid-sagittal sections passing through more medial regions of this structure (not shown). Similarly the posterior tegmental epithelium at E12 expressed ngn2 but not ngn1. Finally, ngn3 expression was even more restricted than that of the other genes, being mostly limited to the hypothalamic region at E12 (data not shown). Expression of ngn3 in this region was mutually exclusive with that of the other two ngn's.

Interestingly, we did not observe major brain regions that express high levels of ngn1 but not ngn2 mRNAs. However, this was indeed observed in the periphery: for example, the trigeminal ganglion and olfactory epithelium expressed ngn1 but not ngn2. Conversely, the retina and IX$^{th}$ cranial ganglion expressed ngn2 but not ngn1. Within the facio-accoustic ganglion complex, ngn1 was expressed in the epithelium of the otic vesicle and in the accoustic component of the facio-accoustic complex (the future vestibulo-cochlear ganglion (VIII$^{th}$ g)) whereas ngn2 was expressed by the facial component of the facio-accoustic complex (the future geniculate ganglion (VII$^{th}$ g)). These examples of complementarity, taken together with their sequence similarity, suggest that ngn1, 2 and 3 may play similar roles in different regions, lineages or sensory organs of the CNS and PNS.

NeuroD Expression Follows that of the Neurogenins in Many Regions and Lineages

In contrast to the more restricted expression domains of the ngn's, neuroD expression encompasses essentially all of the brain areas and peripheral ganglia and sense organs that express ngn1, 2 or 3. Thus, for example, in the hindbrain neuroD expression spans the region of neuroepithelium that expresses ngn1 and ngn2. In the hypothalamus, neuroD was expressed within the region that expresses ngn3. Similarly, in the periphery all of the structures examined express neuroD irrespective of whether they expressed ngn or ngn2.

As reported previously for ngn1 (Ma et al., 1996), within many of the regions or structures where their expression overlaps, neuroD was expressed at a later step in neuronal differentiation than were the neurogenins. This was seen most clearly in cortex, where neuroD mRNA was displaced laterally towards the pial surface, which contained newly-differentiated post mitotic neuroblasts, while ngn1 and ngn2 were expressed in the ventricular and subventricular zones which contain proliferating neural precursors. Other examples of such sequential expression were seen in the hindbrain and the hypothalamus. Apparent exceptions to this rule were seen in the olfactory epithelium and retina, where the expression of both ngn's was detected in laminae that also expressed neuroD; however this apparent lack of laminar separation may simply reflect the relative thinness of these developing sensory epithelia. In the PNS, the lack of a laminar structure makes it impossible to infer sequential expression from spatial segregation. However, analysis of expression at different ages indicated that ngn1 and ngn2 were detected in several cranial sensory ganglia (e.g., IX$^{th}$, VII$^{th}$) at stages when neuroD mRNA was not yet detectable (data not shown). The sequential expression of various neurogenins and neuroD in the mammalian nervous system is consistent with the fact that in Xenopus, X-ngnr-1 functions upstream of, and activates expression of, XneuroD (Ma et al., 1996).

ngn3 is Expressed in Pancreatic Islet Cell Progenitors

As neuroD is also expressed in the pancreas where it is thought to activate expression of islet cell-specific genes (Naya, et al., (1995). Genes & Dev. 9, 1009-1019), we sought to determine whether by analogy to the nervous system there might be members of the ngn subfamily expressed earlier than neuroD in this peripheral endocrine tissue. At E12, when only relatively weak expression of neuroD was detected, strong expression of ngn3 was observed in cells at a similar position on adjacent serial sections. Expression of ngn1 and ngn2 mRNAs was not detected. Expression of ngn3 in the pancreas persisted through at least E14, the latest stage examined, when it identified clusters of apparent islet cells also expressing neuroD. While our data do not directly demonstrate co-expression of these two genes in the same cells, by analogy to the nervous system it seems likely that ngn3 functions upstream of neuroD in a cascade controlling islet cell development.

Sequential and Regionally-Restricted Expression of Different bHLH Factors During Mammalian Neurogenesis Diversity among bHLH factors is thought to subserve different developmental events in different lineages, which occur both in series and in parallel (Jan and Jan, (1993). Cell. 75, 827-830; Weintraub, H. (1993). Cell. 75, 1241-1244). The data presented here are entirely consistent with this idea: different members of the ngn subfamily are expressed in different regions or lineages of the nervous system, while neuroD is expressed downstream of the ngn's in most of these regions. This apparent cascade relationship extends to the endocrine pancreas, where ngn3 seems to be expressed upstream of neuroD. While it is currently difficult to directly demonstrate sequential expression of individual ngn's and neuroD within the same cell lineage, it seems likely by analogy to Xenopus (Ma et al., 1996) that this is indeed the case. Not only is X-ngnr-1 able to activate XneuroD, but mouse ngn1 has been demonstrated to do so in Xenopus, as well (Ma et al., 1996). As ngn2 is even more closely related to X-ngnr-1 than is ngn1, it is likely that NGN2 is also an upstream activator of neuroD; by extension, the same may hold true for ngn3.

Although we have emphasized the striking convergence of different ngn's onto neuroD, additional neuroD-like genes have been identified in this and in other studies (Kume, et al., (1996). Biochem. Biophys. Res. Commun. 219, 526-530; Yasunami et al., (1996) Bicochem. Biophys. Res. Comm. 220, 754-758). As targeted mutations in the neuroD gene in mice interfere with pancreatic but not neuronal development (Lee et al., personal communication), it seems likely that at least some of these neuroD-related genes are functionally-redundant with neuroD itself and therefore that their expression must partially overlap. In that case, different ngn's may activate multiple neuroD-like genes in at least some regions.

In Drosophila, five positive-acting bHLH factors have been identified which promote neurogenesis (Jan and Jan, 1993), and a similar number of positive bHLH factors have been implicated in mammalian myogenesis (Olson and Klein, (1994) Genes & Dev. 8, 1-8). In contrast, the number of mammalian neural-specific, putatively positive-acting bHLH factors is at least three times as large (for review, see (Guillemot, 1995)). (A growing subfamily of negative-acting bHLH factors related to Drosophila hairy and enhancer of split (Sasai, et al., (1992). Genes & Dev. 6, 2620-2634) is not included in this calculation). Why are so many bHLH genes necessary in the mammalian nervous system? Evidence from Drosophila suggests that different proneural genes specify not only the neural fate per se (Campuzano and Modolell, (1992) Trends Genet. 8, 202-208.), but also different neural precursor identities (Jarman, et al., (1993b). Cell. 73, 1307-1321; Skeath and Doe, (1996) Curr. Biol. 6, 1146-1152). Thus the relatively large number of atonal-related bHLH genes may reflect the great diversity of cell types in the mammalian nervous system. It is important to emphasize that the domains of ngn expression exclude large regions which instead express Mash1 (Ma, et al., in preparation). In this respect, it is curious that a similar extent of diversity has not yet been observed for the Mash-related subfamily, only one member of which is specifically expressed in the mammalian nervous system (Guillemot et al., (1994) Nature 371, 333-336; Johnson et al., (1990) Nature 346, 858-861). Whether this reflects technical or rather biological factors remains to be determined.

As in muscle (for review, see (Weintraub, 1993)), the multiplicity of neural bHLH genes also leads to partial functional redundancy. Thus, mutations in neuroD have no apparent neural phenotype (J. Lee, personal communication), and a targeted disruption of Mash1 affects the PNS but not the CNS (Guillemot, et al., (1993). Cell. 75, 463-476), despite the fact that this latter gene is widely expressed in the brain and spinal cord (Guillemot and Joyner, (1993) Mech. Devel. 42, 171-185; Lo et al., 1991). This apparent functional redundancy may arise from cross-regulatory interactions between related bHLH genes, as demonstrated for achaete-scute in Drosophila (Martinez and Modolell, (1991) Science 251, 1485-1487) and the myogenic bHLH genes in mammals (for review see (Weintraub, 1993)). The overlapping expression of ngn1 and ngn2 in some brain regions (e.g., cortex) may similarly reflect such cross-regulation, and suggests that these two genes may exhibit partial functional redundancy as well. Single and double mutants in these genes, currently under construction, should resolve this issue.

Overlapping Expression of Neurogenins in the PNS and CNS

Several regions of the CNS and PNS, such as the cortex and DRG, show at least partially-overlapping expression of ngn1 and ngn2. The sensitivity and resolution of double-label in situ hybridization have been insufficient, at least in our hands, to resolve the issue of whether these two genes are expressed in the same cells, or in distinct but intermingled cell populations. As mentioned above, the precedent for cross-regulatory interactions between related bHLH genes argues for the former interpretation. However, there are also several reasons to consider the latter possibility as well. First, expression of the two genes is not obligatorily coupled: we have demonstrated many regions which express one gene but not the other. Second, in those places where overlap does occur, it is often incomplete: thus in the cortex and hindbrain the boundaries of ngn1 and ngn2 expression are distinct. Third, all of the regions or structures where ngn1 and ngn2 expression overlaps are known to contain phenotypically distinct but intermingled neuronal cell types (Ramon y Cajal, (1995) Histology of the nervous system of man and vertebrates, Oxford University Press).

A final reason is the precedent provided by recent revisions in our understanding of the roles that diverse bHLH factors play in myogenesis (Braun et al., (1994) Development 120, 3083-3092; Patapoutian et al., (1995) Development 121, 3347-3358; Smith et al., (1994) J. Cell Biol. 127, 95-105). Initially, myf5, myoD and myogenin were all thought to be sequentially expressed in a common myogenic cell population within the somites (for review, see (Lyons, (1994) Am. Zool. 34, 305-312)). Subsequent work has revealed, however, that this is not the case: rather, myf5 and myoD are expressed by two distinct myoblast populations (Braun and Arnold, 1996), both of which subsequently express myogenin (Smith et al., 1994). Moreover, expression of myf5 and myoD in these two lineages initiates at different times, so that myogenin has already been expressed in the myf5-dependent lineage before myoD expression has been initiated in the other lineage. In the same way, the sequential but overlapping expression of ngn1 and ngn2 in developing sensory ganglia could reflect their expression in distinct sublineages on different schedules. If so, then the expression of these two genes would provide the first evidence that the lineages that generate different sensory neuron subtypes (Snider, (1994) Cell 77, 627-638) are segregated from a very early stage.

The idea that ngn1 and ngn2 are involved in the specification of different sensory neuron subtypes is further suggested by their pattern of expression in cranial sensory ganglia. We have shown that several of these ganglia express ngn2 but not ngn1, e.g., the $VII^{th}$ and $IX^{th}$ ganglia. Interestingly, the neurons in these ganglia are primarily derived from the epibranchial placodes (Noden, 1993), which also express high levels of ngn2 (but not ngn1). Taken together, these facts are consistent with the idea that the ngn2-expressing cells in these cranial ganglia represent placode-derived neuronal precursors. Other cranial ganglia, however, such as the $V^{th}$ (trigeminal), express ngn1 but not ngn2. Interestingly, these other ganglia contain crest-derived as well as placode-derived neurons (Le Douarin, (1982) The Neural Crest, Cambridge University Press), and it is intriguing to consider that in such dual-origin ganglia ngn1 may be expressed exclusively by crest-derived neuronal precursors. Alternatively, ngn1 and ngn2 might define different sensory sublineages irrespective of their placodal vs. crest origin. Whatever the case, expression of ngn1 and 2 in different cranial sensory sublineages would be consistent with the idea that these genes mark distinct sublineages in trunk sensory ganglia as well.

Cryptic Cellular Heterogeneity Revealed by Expression of the Neurogenins

In addition to their potential importance in understanding the molecular control of neurogenesis, the ngn's may provide useful markers of specific neural progenitor subpopulations for cellular studies of neurogenesis. This is seen in the developing spinal cord where, for example, ngn 1, 2 and 3 each define distinct groups of cells within the VZ, at different positions along the dorso-ventral axis. The developmental significance of these cell groups is not clear, but they indicate that the VZ of the spinal cord is patterned from very early developmental stages. The ngn's may thus provide early markers of responses to inductive signals which are thought to pattern this axis of the spinal cord (Basler et al., (1993) Cell in press; Liem et al., (1995) Cell 82, 969-979; Yamada et al., (1993) Cell 73, 673-686).

Similarly, in the neural crest ngn2 mRNA abundance appears to differ between thoracolumbar and cranial regions. This suggests that there may be positional differences in early migrating neural crest populations, even caudal to the hindbrain crest which is known to be heterogeneous (Hunt and Krumlauf, (1991) Cell 66, 1075-1078). In the trunk region, moreover, ngn2 is expressed in migrating crest and early sensory ganglia but is never detected in autonomic derivatives (which instead express Mash1 (Lo et al., 1991)). This is consistent with the idea (Le Douarin, (1986) Science 231, 1515-1522) that the sensory and autonomic lineages of the crest segregate early in migration. ngn2 may therefore provide a useful marker to understand the control of this early lineage segregation event. In this way, the identification of the ngns may provide a new window into the early origins of neuronal diversity.

Sequential and Regionally-Restricted Expression of Different bHLH Factors During Mammalian Neurogenesis Diversity among bHLH factors is thought to subserve different developmental events in different lineages, which occur both in series and in parallel (Jan and Jan, 1993; Weintraub, 1993). The data presented here are entirely consistent with this idea: different members of the ngn subfamily are expressed in different regions or lineages of the nervous system, while neuroD is expressed downstream of the ngn's in most of these regions. This apparent cascade relationship extends to the endocrine pancreas, where ngn3 seems to be expressed upstream of neuroD. While it is currently difficult to directly demonstrate sequential expression of individual ngn's and neuroD within the same cell lineage, it seems likely by analogy to *Xenopus* (Ma et al., 1996) that this is indeed the case. Not only is X-ngnr-1 able to activate XneuroD, but mouse ngn1 has been demonstrated to do so in *Xenopus*, as well (Ma et al., 1996). As ngn2 is even more closely related to X-ngnr-1 than is ngn1, it is likely that NGN2 is also an upstream activator of neuroD; by extension, the same may hold true for ngn3.

Although we have emphasized the striking convergence of different ngn's onto neuroD, additional neuroD-like genes have been identified in this and in other studies (Kume et al., 1996; McCormick et al., 1996; Yasunami et al., (1996) Biochem. Biophys. Res. Comm. 220, 754-758). As targeted mutations in the neuroD gene in mice interfere with pancreatic but not neuronal development (Lee et al., personal communication), it seems likely that at least some of these neuroD-related genes are functionally-redundant with neuroD itself and therefore that their expression must partially overlap. In that case, different ngn's may activate multiple neuroD-like genes in at least some regions.

In *Drosophila*, five positive-acting bHLH factors have been identified which promote neurogenesis (Jan and Jan, 1993), and a similar number of positive bHLH factors have been implicated in mammalian myogenesis (Olson and Klein, 1994). In contrast, the number of mammalian neural-specific, putatively positive-acting bHLH factors is at least three times as large (for review, see (Guillemot, (1995) Biol. Cell. 84, 3-6). (A growing subfamily of negative-acting bHLH factors related to *Drosophila* hairy and enhancer of split (Sasai et al., (1992) Genes & Dev. 6, 2620-2634) is not included in this calculation). Why are so many bHLH genes necessary in the mammalian nervous system? Evidence from *Drosophila* suggests that different proneural genes specify not only the neural fate per se (Campuzano and Modolell, 1992), but also different neural precursor identities (Jarman et al., 1993b; Skeath and Doe, 1996). Thus the relatively large number of atonal-related bHLH genes may reflect the great diversity of cell types in the mammalian nervous system. It is important to emphasize that the domains of ngn expression exclude large regions which instead express Mash1 (Ma, et al., in preparation). In this respect, it is curious that a similar extent of diversity has not yet been observed for the Mash-related subfamily, only one member of which is specifically expressed in the mammalian nervous system (Guillemot et al., 1994; Johnson et al., 1990). Whether this reflects technical or rather biological factors remains to be determined.

As in muscle (for review, see (Weintraub, 1993)), the multiplicity of neural bHLH genes also leads to partial functional redundancy. Thus, mutations in neuroD have no apparent neural phenotype (J. Lee, personal communication), and a targeted disruption of Mash1 affects the PNS but not the CNS (Guillemot et al., 1993), despite the fact that this latter gene is widely expressed in the brain and spinal cord (Guillemot and Joyner, 1993; Lo et al., 1991). This apparent functional redundancy may arise from cross-regulatory interactions between related bHLH genes, as demonstrated for achaete-scute in *Drosophila* (Martinez and Modolell, 1991) and the myogenic bHLH genes in mammals (for review see (Weintraub, 1993)). The overlapping expression of ngn1 and ngn2 in some brain regions (e.g., cortex) may similarly reflect such cross-regulation, and suggests that these two genes may exhibit partial functional redundancy as well. Single and double mutants in these genes, currently under construction, should resolve this issue.

Overlapping Expression of Neurogenins in the PNS and CNS

Several regions of the CNS and PNS, such as the cortex and DRG, show at least partially-overlapping expression of ngn1 and ngn2. The sensitivity and resolution of double-label in situ hybridization have been insufficient, at least in our hands, to resolve the issue of whether these two genes are expressed in the same cells, or in distinct but intermingled cell populations. As mentioned above, the precedent for cross-regulatory interactions between related bHLH genes argues for the former interpretation. However, there are also several reasons to consider the latter possibility as well. First, expression of the two genes is not obligatorily coupled: we have demonstrated many regions which express one gene but not the other. Second, in those places where overlap does occur, it is often incomplete: thus in the cortex and hindbrain the boundaries of ngn1 and ngn2 expression are distinct. Third, all of the regions or structures where ngn1 and ngn2 expression overlaps are known to contain phenotypically distinct but intermingled neuronal cell types (Ramon y Cajal, 1995).

A final reason is the precedent provided by recent revisions in our understanding of the roles that diverse bHLH factors play in myogenesis (Braun and Arnold, 1996; Braun et al., 1994; Patapoutian et al., 1995; Smith et al., 1994). Initially, myf5, myoD and myogenin were all thought to be sequentially expressed in a common myogenic cell population within the somites (for review, see (Lyons, 1994)). Subsequent work has revealed, however, that this is not the case: rather, myf5 and myoD) are expressed by two distinct myoblast populations (Braun and Arnold, 1996), both of which subsequently express myogenin (Smith et al., 1994). Moreover, expression of myf5 and myoD in these two lineages initiates at different times, so that myogenin has already been expressed in the myf5-dependent lineage before myoD expression has been initiated in the other lineage. In the same way, the sequential but overlapping expression of ngn1 and ngn2 in developing sensory ganglia could reflect their expression in distinct sublineages on different schedules. If so, then the expression of these two genes would provide the first evidence that the lineages that generate different sensory neuron subtypes (Snider, 1994) are segregated from a very early stage.

The idea that ngn1 and ngn2 are involved in the specification of different sensory neuron subtypes is further suggested by their pattern of expression in cranial sensory ganglia. We have shown that several of these ganglia express ngn2 but not ngn1, e.g., the VII[th] and IX[th] ganglia. Interestingly, the neurons in these ganglia are primarily derived from the epibranchial placodes (Noden, 1993), which also express high levels of ngn2 (but not ngn1). Taken together, these facts are consistent with the idea that the ngn2-expressing cells in these cranial ganglia represent placode-derived neuronal precursors. Other cranial ganglia, however, such as the V[th] (trigeminal), express ngn1 but not ngn2. Interestingly, these other ganglia contain crest-derived as well as placode-derived neurons (Le Douarin, 1982), and it is intriguing to consider that in such dual-origin ganglia ngn1 may be expressed exclusively by crest-derived neuronal precursors. Alternatively, ngn1 and ngn2 might define different sensory sublineages irrespective of their placodal vs. crest origin. Whatever the case, expression of ngn1 and 2 in different cranial sensory sublineages would be consistent with the idea that these genes mark distinct sublineages in trunk sensory ganglia as well.

Cryptic Cellular Heterogeneity Revealed by Expression of the Neurogenins

In addition to their potential importance in understanding the molecular control of neurogenesis, the ngn's may provide useful markers of specific neural progenitor subpopulations for cellular studies of neurogenesis. This is seen in the developing spinal cord where, for example, ngn1, 2 and 3 each define distinct groups of cells within the VZ, at different positions along the dorso-ventral axis. The developmental significance of these cell groups is not clear, but they indicate that the VZ of the spinal cord is patterned from very early developmental stages. The ngn's may thus provide early markers of responses to inductive signals which are thought to pattern this axis of the spinal cord (Basler et al., 1993; Liem et al., 1995; Yamada et al., 1993).

Similarly, in the neural crest ngn2 mRNA abundance appears to differ between thoracolumbar and cranial regions. This suggests that there may be positional differences in early migrating neural crest populations, even caudal to the hindbrain crest which is known to be heterogeneous (Hunt and Krumlauf, 1991). In the trunk region, moreover, ngn2 is expressed in migrating crest and early sensory ganglia but is never detected in autonomic derivatives (which instead express Mash1 (Lo et al., 1991)). This is consistent with the idea (Le Douarin, 1986) that the sensory and autonomic lineages of the crest segregate early in migration. ngn2 may therefore provide a useful marker to understand the control of this early lineage segregation event. In this way, the identification of the ngns may provide a new window into the early origins of neuronal diversity.

Sequential and Regionally-Restricted Expression of Different bHLH Factors During Mammalian Neurogenesis Diversity among bHLH factors is thought to subserve different developmental events in different lineages, which occur both in series and in parallel (Jan and Jan, 1993; Weintraub, 1993). The data presented here are entirely consistent with this idea: different members of the ngn subfamily are expressed in different regions or lineages of the nervous system, while neuroD is expressed downstream of the ngn's in most of these regions. This apparent cascade relationship extends to the endocrine pancreas, where ngn3 seems to be expressed upstream of neuroD. While it is currently difficult to directly demonstrate sequential expression of individual ngn's and neuroD within the same cell lineage, it seems likely by analogy to *Xenopus* (Ma et al., 1996) that this is indeed the case. Not only is X-ngnr-1 able to activate XneuroD, but mouse ngn1 has been demonstrated to do so in *Xenopus*, as well (Ma et al., 1996). As ngn2 is even more closely related to X-ngnr-1 than is ngn1 (FIG. 2), it is likely that NGN2 is also an upstream activator of neuroD; by extension, the same may hold true for ngn3.

Although we have emphasized the striking convergence of different ngn's onto neuroD, additional neuroD-like genes have been identified in this and in other studies (Kume et al., 1996; McCormick et al., 1996; Yasunami et al., 1996). As targeted mutations in the neuroD gene in mice interfere with pancreatic but not neuronal development (Lee et al., personal communication), it seems likely that at least some of these neuroD-related genes are functionally-redundant with neuroD itself and therefore that their expression must partially overlap. In that case, different ngn's may activate multiple neuroD-like genes in at least some regions.

In *Drosophila*, five positive-acting bHLH factors have been identified which promote neurogenesis (Jan and Jan, 1993), and a similar number of positive bHLH factors have been implicated in mammalian myogenesis (Olson and Klein, 1994). In contrast, the number of mammalian neural-specific, putatively positive-acting bHLH factors is at least three times as large (for review, see (Guillemot, 1995)). (A growing subfamily of negative-acting bHLH factors related to *Drosophila* hairy and enhancer of split (Sasai et al., 1992) is not included in this calculation). Why are so many b-bHLH genes necessary in the mammalian nervous system? Evidence from *Drosophila* suggests that different proneural genes specify not only the neural fate per se (Campuzano and Modolell, 1992), but also different neural precursor identities (Jarman et al., 1993b; Skeath and Doe, 1996). Thus the relatively large number of atonal-related bHLH genes may reflect the great diversity of cell types in the mammalian nervous system. It is important to emphasize that the domains of ngn expression exclude large regions which instead express Mash1 (Ma, et al., in preparation). In this respect, it is curious that a similar extent of diversity has not yet been observed for the Mash-related subfamily, only one member of which is specifically expressed in the mammalian nervous system (Guillemot et al., 1994; Johnson et al., 1990). Whether this reflects technical or rather biological factors remains to be determined.

As in muscle (for review, see (Weintraub, 1993)), the multiplicity of neural bHLH genes also leads to partial functional redundancy. Thus, mutations in neuroD have no apparent neural phenotype (J. Lee, personal communication), and a targeted disruption of Mash1 affects the PNS but not the CNS (Guillemot et al., 1993), despite the fact that this latter gene is widely expressed in the brain and spinal cord (Guillemot and Joyner, 1993; Lo et al., 1991). This apparent functional redundancy may arise from cross-regulatory interactions between related bHLH genes, as demonstrated for achaete-scute in *Drosophila* (Martinez and Modolell, 1991) and the myogenic bHLH genes in mammals (for review see (Weintraub, 1993)). The overlapping expression of ngn1 and ngn2 in some brain regions (e.g., cortex) may similarly reflect such cross-regulation, and suggests that these two genes may exhibit partial functional redundancy as well. Single and double mutants in these genes, currently under construction, should resolve this issue.

Overlapping Expression of Neurogenins in the PNS and CNS

Several regions of the CNS and PNS, such as the cortex and DRG, show at least partially-overlapping expression of ngn1 and ngn2. The sensitivity and resolution of double-label in situ hybridization have been insufficient, at least in our hands, to resolve the issue of whether these two genes are expressed in the same cells, or in distinct but intermingled cell populations. As mentioned above, the precedent for cross-regulatory interactions between related bHLH genes argues for the former interpretation. However, there are also several reasons to consider the latter possibility as well. First, expression of the two genes is not obligatorily coupled: we have demonstrated many regions which express one gene but not the other. Second, in those places where overlap does occur, it is often incomplete: thus in the cortex and hindbrain the boundaries of ngn1 and ngn2 expression are distinct. Third, all of the regions or structures where ngn 1 and ngn2 expression overlaps are known to contain phenotypically distinct but intermingled neuronal cell types (Ramon y Cajal, 1995).

A final reason is the precedent provided by recent revisions in our understanding of the roles that diverse bHLH factors play in myogenesis (Braun and Arnold, 1996; Braun et al., 1994; Patapoutian et al., 1995; Smith et al., 1994). Initially, myf5, myoD and myogenin were all thought to be sequentially expressed in a common myogenic cell population within the somites (for review, see (Lyons, (1994) Am. Zool. 34, 305-312). Subsequent work has revealed, however, that this is not the case: rather, myf5 and myoD are expressed by two distinct myoblast populations (Braun and Arnold, 1996), both of which subsequently express myogenin (Smith et al., 1994). Moreover, expression of myf5 and myoD in these two lineages initiates at different times, so that myogenin has already been expressed in the myf5-dependent lineage before myoD expression has been initiated in the other lineage. In the same way, the sequential but overlapping expression of ngn1 and ngn2 in developing sensory ganglia, for example, could reflect their expression in distinct sublineages on different schedules. If so, then the expression of these two genes would provide the first evidence that the lineages that generate different sensory neuron subtypes (Snider, 1994) are segregated from a very early stage.

The idea that ngn1 and ngn2 are involved in the specification of different sensory neuron subtypes is further suggested by their pattern of expression in cranial sensory ganglia. We have shown that several of these ganglia express ngn2 but not ngn1, e.g., the $VII^{th}$ and $IX^{th}$ ganglia. Interestingly, the neurons in these ganglia are primarily derived from the epibranchial placodes (Noden, 1993), which also express high levels of ngn2 (but not ngn1). Taken together, these facts are consistent with the idea that the ngn2-expressing cells in these cranial ganglia represent placode-derived neuronal precursors. Other cranial ganglia, however, such as the $V^{th}$ (trigeminal), express ngn1 but not ngn2. Interestingly, these other ganglia contain crest-derived as well as placode-derived neurons (Le Douarin, 1982), and it is intriguing to consider that in such dual-origin ganglia ngn1 may be expressed exclusively by crest-derived neuronal precursors. Alternatively, ngn1 and ngn2 might define different sensory sublineages irrespective of their placodal vs. crest origin. Whatever the case, expression of ngn1 and 2 in different cranial sensory sublineages would be consistent with the idea that these genes mark distinct sublineages in trunk sensory ganglia as well.

Cryptic Cellular Heterogeneity Revealed by Expression of the Neurogenins

In addition to their potential importance in understanding the molecular control of neurogenesis, the ngn's may provide useful markers of specific neural progenitor subpopulations for cellular studies of neurogenesis. This is seen in the developing spinal cord where, for example, ngn1, 2 and 3 each define distinct groups of cells within the VZ, at different positions along the dorso-ventral axis. The developmental significance of these cell groups is not clear, but they indicate that the VZ of the spinal cord is patterned from very early developmental stages. The ngn's may thus provide early markers of responses to inductive signals which are thought to pattern this axis of the spinal cord (Basler et al., 1993; Liem et al., (1995); Yamada et al., 1993).

Similarly, in the neural crest ngn2 mRNA abundance appears to differ between thoracolumbar and cranial regions. This suggests that there may be positional differences in early migrating neural crest populations, even caudal to the hindbrain crest which is known to be heterogeneous (Hunt and Krumlauf, 1991). In the trunk region, moreover, ngn2 is expressed in migrating crest and early sensory ganglia but is never detected in autonomic derivatives (which instead express Mash (Lo et al., 1991)). This is consistent with the idea (Le Douarin, 1986) that the sensory and autonomic lineages of the crest segregate early in migration. ngn2 may therefore provide a useful marker to understand the control of this early lineage segregation event. In this way, the identification of the ngns may provide a new window into the early origins of neuronal diversity.

BIBLIOGRAPHY

Akazawa, et al., (1995) J. Biol. Chem. 270, 8730-8738.
Akazawa, et al., (1992) J. Biol. Chem. 21879-21885.
Alonso et al., EMBO J. 1988 7:2585
Amon, A. (1996) Cell. 84, 651-654.
Artavanis-Tsakonas, et al., (1995) Science. 268, 225-232.
Bartholomaa, et al., (1994) Mech. Devel. 48, 217-228.
Basler et al., 1993 Cell 73:687
Birren et al., 1993 Development 119:597
Blaugrund et al., 1996 Development 122:309
Bobola, et al., (1996) Cell. 84, 699-710.
Brand, et al., (1993) Development. 119, 1-17.
Braun et al., 1996 EMBO J. 15:310
Braun et al., 1994 Development 120:3083
Campuzano, et al., (1992) Trends Genet. 8, 202-208.
Chitnis, et al., (1995) Nature. 375, 761-766.
Chitnis, et al., (1996) Development. in press,
Chitnis, A. B. (1995). Mol. Cell. Neurosci. 6, 311-321.
Chomczynski et al. (1987) Anal. Biochem. 162:156
Cserjesi et al., 1995 Development 121:1099
Coffman, et al., (1990) Science. 249, 1438-1441.
Coffman, et al., (1993) Cell. 73, 659-671.
Cubas, et al., (1991) Genes & Dev. 5, 996-1008.
Dominguez, et al., (1993) EMBO J. 12, 2049-2060.
Ferreiro, et al., (1994) Development. 120, 3649-3655.
Ferreiro, et al., (1992) Mech. Development. 40, 25-36.
Garrell et al., 1991 BioEssays 13:493
Ghysen, et al., (1993) Genes & Dev. 7, 723-733.
Guillemot 1995 Biol. Cell. 84:3-6
Guillemot, et al., (1993) Mech. Devel. 42, 171-185.
Guillemot, et al., (1993) Cell. 75, 463-476.
Hinz, et al., (1994) Cell. 76, 77-88.
Hunt et al., Cell 1991 66:1075
Ishibashi, et al., (1993) Eur. J. Biochem. 215, 645-652.
Jan, Y. N. and Jan, L. Y. (1993) Cell. 75, 827-830.
Jan, Y. N. and Jan, L. Y. (1994) Annu. Rev. Genet. 28:373-393
Jarman, et al., (1993a) Development. 119, 19-29.
Jarman, et al., (1993b) Cell. 73, 1307-1321.
Jarman et al., 1994 Nature 369:398
Johnson, et al., (1990) Nature. 346, 858-861.
Kintner, et al., (1987) Development. 99, 311-325.
Kopan, et al., (1994) Development. 120, 2385-2396.
Kozak, M. (1984) 12, 857-872.
Kume, et al., (1996) Biochem. Biophys. Res. Res. Commun. 219, 526-530.
Kunisch, et al., (1994) Proc. Natl. Acad. Sci. U.S.A. 91, 10139-10143.
Lamb, et al., (1993) Science. 262, 713-718.
Le Dourin et al., 1982 The Neural Crest. Cambridge Univ. Press
Le Dourin 1986 Science 231:1515
Lee, et al., (1995) Science. 268, 836-844.
Liem et al., 1995 Cell 82:969
Lo, et al., (1991) Genes & Dev. 5, 1524-1537.
Lyons 1994 Am. Zool. 34:305
Ma et al., 1996 Cell 87:43
Martinez et al., 1991: Science 251:1485
McCormick et al., 1996: Mol. Cell. Biol. 16:5792
Meyer et al., 1995 Nature 378:386
Naya, et al., (1995) Genes & Dev. 9, 1009-1019.
Noden et al., 1993 J. Neurobiol. 24:248
Nye, et al., (1994) Development. 120, 2421-2430.
Olson, et al., (1994) Genes & Dev. 8, 1-8.
Patapoutian et al., 1995 Development 121:3347
Ramon y Cajal 1995: History of the Nervous System of Man and Vertebrates, Oxford University Press, New York.
Saito, et al., (1995) Mol. Cell. Neurosci. 6, 280-292.
Sasai, et al., (1992) Genes & Dev. 6, 2620-2634.
Sasai, et al., (1995) Nature. 376, 333-336.
Shimizu, et al., (1995) Eur. J. Biochem. 229, 239-248.
Sil, et al., (1996) Cell. 84, 711-722.
Skeath et al., 1996 Curr. Biol. 6:1146
Smith, et al., (1992) Cell. 70, 829-840.
Snider et al., 1994 J. Cell. Bio. 127:95
Sommer, et al., (1995) Neuron. 15, 1245-1258.
Struhl, et al., (1993) Cell. 74, 331-345.
Turner, et al., (1994) Genes Dev. 8, 1434-1447.
Villares, et al., (1987) Cell. 50, 415-424.
Weintraub, H. (1993). Cell. 75, 1241-1244.
Wilkinson 1992 in In Situ Hybridization: A Practical Approach, IRL Press, Oxford
Yamada et al., 1993 Cell 73:673
Yasunami et al., 1996 Biochem Biophys. Res. Comm. 220: 754
Zimmerman, et al., (1993) Development. 119, 221-232.

SEQUENCE LISTING

```
<160> NUMBER OF SEQ ID NOS: 31

<210> SEQ ID NO 1
<211> LENGTH: 245
<212> TYPE: PRT
<213> ORGANISM: Rattus sp.

<400> SEQUENCE: 1

Met Pro Ala Pro Leu Glu Thr Cys Leu Ser Asp Leu Asp Cys Ala Ser
 1               5                  10                  15

Ser Asn Ser Gly Ser Asp Leu Ser Ser Phe Leu Thr Asp Glu Glu Asp
                20                  25                  30

Cys Ala Arg Leu Gln Pro Leu Ala Ser Thr Ser Gly Leu Ser Val Pro
            35                  40                  45
```

Ala Arg Arg Ser Ala Pro Thr Leu Ser Gly Ala Ser Asn Val Pro Gly
        50                  55                  60

Gly Gln Asp Glu Glu Gln Glu Arg Arg Arg Arg Gly Arg Ala Arg
65                  70                  75                  80

Val Arg Ser Glu Ala Leu Leu His Ser Leu Arg Arg Ser Arg Arg Val
                85                  90                  95

Lys Ala Asn Asp Arg Glu Arg Asn Arg Met His Asn Leu Asn Ala Ala
                100                 105                 110

Leu Asp Ala Leu Arg Ser Val Leu Pro Ser Phe Pro Asp Thr Lys
            115                 120                 125

Leu Thr Lys Ile Glu Thr Leu Arg Phe Ala Tyr Asn Tyr Ile Trp Ala
130                 135                 140

Leu Ala Glu Thr Leu Arg Leu Ala Asp Gln Gly Leu Pro Gly Gly Gly
145                 150                 155                 160

Met Ala Arg Glu Arg Leu Leu Pro Pro Gln Cys Val Pro Cys Leu Pro
                165                 170                 175

Gly Pro Pro Ser Pro Ala Ser Asp Thr Glu Ser Trp Gly Ser Gly Ala
            180                 185                 190

Ala Ala Ser Pro Cys Ala Thr Val Ala Ser Pro Leu Ser Asp Pro Ser
            195                 200                 205

Ser Pro Ser Ala Ser Glu Asp Phe Thr Tyr Gly Pro Gly Gly Pro Leu
    210                 215                 220

Phe Ser Phe Pro Gly Leu Pro Lys Asp Leu Leu His Thr Thr Pro Cys
225                 230                 235                 240

Phe Ile Pro Tyr His
                245

<210> SEQ ID NO 2
<211> LENGTH: 214
<212> TYPE: PRT
<213> ORGANISM: Xenopus sp.

<400> SEQUENCE: 2

Met Val Leu Leu Lys Cys Glu Tyr Arg Asp Glu Glu Glu Asp Leu Thr
1               5                   10                  15

Ser Ala Ser Pro Cys Ser Val Thr Ser Ser Phe Arg Ser Pro Ala Thr
                20                  25                  30

Gln Thr Cys Ser Ser Asp Asp Glu Gln Leu Leu Ser Pro Thr Ser Pro
            35                  40                  45

Gly Gln His Gln Gly Glu Glu Asn Ser Pro Arg Cys Arg Arg Ser Arg
    50                  55                  60

Gly Arg Ala Gln Gly Lys Ser Gly Glu Thr Val Leu Lys Ile Lys Lys
65                  70                  75                  80

Thr Arg Arg Val Lys Ala Asn Asn Arg Glu Arg Asn Arg Met His Asn
                85                  90                  95

Leu Asn Ser Ala Leu Asp Ser Leu Arg Glu Val Leu Pro Ser Leu Pro
                100                 105                 110

Glu Asp Ala Lys Leu Thr Lys Ile Glu Thr Leu Arg Phe Ala Tyr Asn
            115                 120                 125

Tyr Ile Trp Ala Leu Ser Glu Thr Leu Arg Leu Gly Asp Pro Val His
130                 135                 140

Arg Ser Ala Ser Thr Pro Ala Ala Ala Ile Leu Val Gln Asp Ser Ser
145                 150                 155                 160

Ser Ser Gln Ser Pro Ser Trp Ser Cys Ser Ser Ser Pro Ser Ser Ser
                165                 170                 175

```
Cys Cys Ser Phe Ser Pro Ala Ser Pro Ala Ser Ser Thr Ser Asp Ser
            180                 185                 190

Ile Glu Ser Trp Gln Pro Ser Glu Leu His Leu Asn Pro Phe Met Ser
        195                 200                 205

Ala Ser Ser Ala Phe Ile
        210

<210> SEQ ID NO 3
<211> LENGTH: 57
<212> TYPE: PRT
<213> ORGANISM: Mus musculus

<400> SEQUENCE: 3

Arg Ser Arg Arg Val Lys Ala Asn Asp Arg Glu Arg Asn Arg Met His
  1               5                  10                  15

Asn Leu Asn Ala Ala Leu Asp Ala Leu Arg Ser Val Leu Pro Ser Phe
             20                  25                  30

Pro Asp Asp Thr Lys Leu Thr Lys Ile Glu Thr Leu Arg Phe Ala Tyr
         35                  40                  45

Asn Tyr Ile Trp Ala Leu Ala Glu Thr
 50                  55

<210> SEQ ID NO 4
<211> LENGTH: 57
<212> TYPE: PRT
<213> ORGANISM: Xenopus sp.

<400> SEQUENCE: 4

Lys Thr Arg Arg Val Lys Ala Asn Asn Arg Glu Arg Asn Arg Met His
  1               5                  10                  15

Asn Leu Asn Ser Ala Leu Asp Ser Leu Arg Glu Val Leu Pro Ser Leu
             20                  25                  30

Pro Glu Asp Ala Lys Leu Thr Lys Ile Glu Thr Leu Arg Phe Ala Tyr
         35                  40                  45

Asn Tyr Ile Trp Ala Leu Ser Glu Thr
 50                  55

<210> SEQ ID NO 5
<211> LENGTH: 57
<212> TYPE: PRT
<213> ORGANISM: Mus musculus

<400> SEQUENCE: 5

Lys Leu Arg Arg Met Lys Ala Asn Ala Arg Glu Arg Asn Arg Met His
  1               5                  10                  15

Gly Leu Asn Ala Ala Leu Asp Asn Leu Arg Lys Val Val Pro Cys Tyr
             20                  25                  30

Ser Lys Thr Gln Lys Leu Ser Lys Ile Glu Thr Leu Arg Leu Ala Lys
         35                  40                  45

Asn Tyr Ile Trp Ala Leu Ser Glu Ile
 50                  55

<210> SEQ ID NO 6
<211> LENGTH: 57
<212> TYPE: PRT
<213> ORGANISM: Mus musculus

<400> SEQUENCE: 6

Lys Phe Arg Arg Gln Glu Ala Asn Ala Arg Glu Arg Asn Arg Met His
```

```
            1               5                  10                 15
         Gly Leu Asn Asp Ala Leu Asp Asn Leu Arg Lys Val Val Pro Cys Tyr
                            20                 25                 30

Ser Lys Thr Gln Lys Leu Ser Lys Ile Glu Thr Leu Arg Leu Ala Lys
                            35                 40                 45

Asn Tyr Ile Trp Ala Leu Ser Glu Ile
                            50                 55
```

<210> SEQ ID NO 7
<211> LENGTH: 57
<212> TYPE: PRT
<213> ORGANISM: Rattus sp.

<400> SEQUENCE: 7

```
         Lys Leu Arg Arg Gln Lys Ala Asn Ala Arg Glu Arg Asn Arg Met His
          1               5                  10                 15

Asp Leu Asn Ala Ala Leu Asp Asn Leu Arg Lys Val Val Pro Cys Tyr
                            20                 25                 30

Ser Lys Thr Gln Lys Leu Ser Lys Ile Glu Thr Leu Arg Leu Ala Lys
                            35                 40                 45

Asn Tyr Ile Trp Ala Leu Ser Glu Ile
                            50                 55
```

<210> SEQ ID NO 8
<211> LENGTH: 57
<212> TYPE: PRT
<213> ORGANISM: Mus musculus

<400> SEQUENCE: 8

```
         Lys Asn Arg Arg Leu Ala Ala Asn Ala Arg Glu Arg Arg Arg Met His
          1               5                  10                 15

Gly Leu Asn His Ala Phe Asp Gln Leu Arg Asn Val Ile Pro Ser Phe
                            20                 25                 30

Asn Asn Asp Lys Lys Leu Ser Lys Tyr Glu Thr Leu Gln Met Ala Gln
                            35                 40                 45

Ile Tyr Ile Asn Ala Leu Ser Glu Ile
                            50                 55
```

<210> SEQ ID NO 9
<211> LENGTH: 57
<212> TYPE: PRT
<213> ORGANISM: Drosophila atonal

<400> SEQUENCE: 9

```
         Arg Lys Arg Arg Leu Ala Ala Asn Ala Arg Glu Arg Arg Arg Met Gln
          1               5                  10                 15

Asn Leu Asn Gln Ala Phe Asp Arg Leu Arg Gln Tyr Leu Pro Cys Leu
                            20                 25                 30

Gly Asn Asp Arg Gln Leu Ser Lys His Glu Thr Leu Gln Met Ala Gln
                            35                 40                 45

Thr Tyr Ile Ser Ala Leu Gly Asp Leu
                            50                 55
```

<210> SEQ ID NO 10
<211> LENGTH: 54
<212> TYPE: PRT
<213> ORGANISM: Rattus sp.

<400> SEQUENCE: 10

Val Ala Arg Arg Asn Glu Arg Glu Arg Asn Arg Val Lys Leu Val Asn
1               5                   10                  15

Leu Gly Phe Ala Thr Leu Arg Glu His Val Pro Asn Gly Ala Ala Asn
            20                  25                  30

Lys Lys Met Ser Lys Val Glu Thr Leu Arg Ser Ala Val Glu Tyr Ile
        35                  40                  45

Arg Ala Leu Gln Gln Leu
    50

<210> SEQ ID NO 11
<211> LENGTH: 68
<212> TYPE: PRT
<213> ORGANISM: Drosophila atonal

<400> SEQUENCE: 11

Val Ile Arg Arg Asn Ala Arg Glu Arg Asn Arg Val Lys Gln Val Asn
1               5                   10                  15

Asn Gly Phe Ser Gln Leu Arg Gln His Ile Pro Ala Ala Val Ile Ala
            20                  25                  30

Asp Leu Ser Asn Gly Arg Arg Gly Ile Gly Pro Gly Ala Asn Lys Lys
        35                  40                  45

Leu Ser Lys Val Ser Thr Leu Lys Met Ala Val Glu Tyr Ile Arg Arg
    50                  55                  60

Leu Gln Lys Val
 65

<210> SEQ ID NO 12
<211> LENGTH: 1527
<212> TYPE: DNA
<213> ORGANISM: Rattus sp.

<400> SEQUENCE: 12
atccggagct gatctgatcg ccggcgacat cagtcgggag accagcccgg cgcgtggccc      60
cctgcaggcg aggcgaggag gccaagccca ttccctccct gagcccctgc gatcttccc     120
ggccctcgcg cctgcagcag gcacaggcta gccccgggtc atacggacag taagtgcgct    180
tcgaaggccg tgcactcggc ccacattcaa gccctccaaa cctcccgtcc gtccgtccgt    240
cctgcaacga tgcctgcccc tttggagacc tgtctctctg acctcgactg cgccagcagc    300
aacagcggga gcgacctgtc cagtttcctc accgacgagg aggactgtgc caggctccag    360
cccctagctt ccacctcagg gctgtccgtg ccagcccgca ggagcgcgcc caccctctcc    420
ggggcatcga acgttcccgg tggccaggac gaagagcagg agcggcggcg acggcgaggt    480
cgcgcgcggg tgcggtccga ggcgctgctg cactcgctgc ggaggagccg tcgcgtcaag    540
gccaacgatc gcgagcgcaa ccgtatgcat aacctcaacg ctgcgctgga cgctctgcgc    600
agcgtgctgc cctcgttccc cgacgacacc aagctcacca agattgagac gctgcgcttc    660
gcctacaact acatctgggc cctggctgag acactgcgcc tggcagatca agggctcccg    720
gggggcggtg cccgggagcg cctcctgcct ccgcagtgtg tcccctgcct gcccggtccc    780
ccgagcccgg ccagcgatac agagtcctgg ggctccgggg ccgctgcctc ccctgcgct    840
actgtggcgt caccactctc tgaccccagt agtccctcgg cttcagaaga cttcacctat    900
ggcccgggtg gtccccttt ctcctttcct ggcctgccca agacctcct ccatacgaca    960
ccctgcttca tcccgtacca ctagggcttt gcaagacaac gttaatactt ctttcctgcc   1020
ccagtctatg agcaatagat gggggagccg gctgaagcct cggggagcac ccttacccccc   1080

| | |
|---|---|
| aggtggatgc tgggagcttt aaagagggga gggatacctg accacttgct aggttgccgc | 1140 |
| accctcgctg agaagctgcc cctcggactg tttccccacg cccagcacc gggcccctcc | 1200 |
| tgcccgcccc ccagacgggc tttcggtttt tttttggac ttcctgaact tcacaaaacc | 1260 |
| tcctttgtga ctggctcaga actgacccca gccaccactt cagtgtgatt tggaaaaggg | 1320 |
| acagatgagc ccctgaagac gaggtgaaaa gtcaatttta caatttgtag aactctaatg | 1380 |
| aagaaaaacg agcatgaaaa ttcggtttga gccggctgac aatacaatga aaaggcttaa | 1440 |
| aaaaaaggag acacaaggag tgggcttcat gcattatgga tcccgacccc caccactgtg | 1500 |
| ggcttgctcc cggaagaact gagtgct | 1527 |

```
<210> SEQ ID NO 13
<211> LENGTH: 738
<212> TYPE: DNA
<213> ORGANISM: Mus musculus
<220> FEATURE:
<221> NAME/KEY: CDS
<222> LOCATION: (1)..(732)

<400> SEQUENCE: 13
```

| | |
|---|---|
| atg cct ccc cct ttg gag acc tgc atc tct gat ctc gac tgc tcc agc<br>Met Pro Pro Pro Leu Glu Thr Cys Ile Ser Asp Leu Asp Cys Ser Ser<br>1                  5                   10               15 | 48 |
| agc aac agc agc agc gac ctg tcc agc ttc ctc acc gac gag gag gac<br>Ser Asn Ser Ser Ser Asp Leu Ser Ser Phe Leu Thr Asp Glu Glu Asp<br>                  20                   25                   30 | 96 |
| tgt gcc agg cta cag ccc cta gcc tcc acc tcg ggg ctg tcc gtg cca<br>Cys Ala Arg Leu Gln Pro Leu Ala Ser Thr Ser Gly Leu Ser Val Pro<br>        35                   40                   45 | 144 |
| gcc cgg agg agc gct ccc gcc ctc tcc ggg gca tcg aat gtt ccc ggt<br>Ala Arg Arg Ser Ala Pro Ala Leu Ser Gly Ala Ser Asn Val Pro Gly<br>50                  55                   60 | 192 |
| gcc cag gac gaa gag cag gaa cgg cgg agg cgg cga ggt cgc gct cgg<br>Ala Gln Asp Glu Glu Gln Glu Arg Arg Arg Arg Arg Gly Arg Ala Arg<br>65                  70                   75                   80 | 240 |
| gtg cgg tcc gag gct ctg ctg cac tcc ctg cgg agg agt cgt cgc gtc<br>Val Arg Ser Glu Ala Leu Leu His Ser Leu Arg Arg Ser Arg Arg Val<br>                       85                   90                   95 | 288 |
| aaa gcc aac gat cgc gag cgc aac cgc atg cac aac ctc aac gct gcg<br>Lys Ala Asn Asp Arg Glu Arg Asn Arg Met His Asn Leu Asn Ala Ala<br>                100                 105                 110 | 336 |
| ctg gac gcc ttg cgc agc gtg ctg ccc tcg ttc ccc gac gac acc aag<br>Leu Asp Ala Leu Arg Ser Val Leu Pro Ser Phe Pro Asp Asp Thr Lys<br>115                 120                 125 | 384 |
| ctc acc aag att gag acg ctg cgc ttc gcc tac aac tac atc tgg gcc<br>Leu Thr Lys Ile Glu Thr Leu Arg Phe Ala Tyr Asn Tyr Ile Trp Ala<br>130                 135                 140 | 432 |
| ctg gct gag aca ctg cgc ctg gca gat caa ggg ctc ccc ggg ggc agt<br>Leu Ala Glu Thr Leu Arg Leu Ala Asp Gln Gly Leu Pro Gly Gly Ser<br>145                 150                 155                 160 | 480 |
| gcc cgg gag cgc ctc ctg cct ccg cag tgt gtc ccc tgt ctg ccc ggg<br>Ala Arg Glu Arg Leu Leu Pro Pro Gln Cys Val Pro Cys Leu Pro Gly<br>                       165                 170                 175 | 528 |
| ccc ccg agc ccg gcc agc gac act gag tcc tgg ggt tcc ggg gcc gct<br>Pro Pro Ser Pro Ala Ser Asp Thr Glu Ser Trp Gly Ser Gly Ala Ala<br>                180                 185                 190 | 576 |
| gcc tcc ccc tgc gcc act gtg gca tca cca ctc tct gac ccc agt agt<br>Ala Ser Pro Cys Ala Thr Val Ala Ser Pro Leu Ser Asp Pro Ser Ser<br>195                 200                 205 | 624 |

```
ccc tcg gct tca gaa gac ttc acc tat ggc ccg ggc gat ccc ctt ttc    672
Pro Ser Ala Ser Glu Asp Phe Thr Tyr Gly Pro Gly Asp Pro Leu Phe
    210                 215                 220 tcc ttt cct ggc ctg ccc aaa gac ctg ctc cac acg acg ccc tgt ttc    720
Ser Phe Pro Gly Leu Pro Lys Asp Leu Leu His Thr Thr Pro Cys Phe
225                 230                 235                 240 atc cca tac cac tagtaa                                              738
Ile Pro Tyr His
```

<210> SEQ ID NO 14
<211> LENGTH: 244
<212> TYPE: PRT
<213> ORGANISM: Mus musculus

<400> SEQUENCE: 14

```
Met Pro Pro Pro Leu Glu Thr Cys Ile Ser Asp Leu Asp Cys Ser Ser
1               5                   10                  15

Ser Asn Ser Ser Ser Asp Leu Ser Ser Phe Leu Thr Asp Glu Glu Asp
            20                  25                  30

Cys Ala Arg Leu Gln Pro Leu Ala Ser Thr Ser Gly Leu Ser Val Pro
        35                  40                  45

Ala Arg Arg Ser Ala Pro Ala Leu Ser Gly Ala Ser Asn Val Pro Gly
    50                  55                  60

Ala Gln Asp Glu Glu Gln Glu Arg Arg Arg Arg Gly Arg Ala Arg
65                  70                  75                  80

Val Arg Ser Glu Ala Leu Leu His Ser Leu Arg Arg Ser Arg Val
                85                  90                  95

Lys Ala Asn Asp Arg Glu Arg Asn Arg Met His Asn Leu Asn Ala Ala
            100                 105                 110

Leu Asp Ala Leu Arg Ser Val Leu Pro Ser Phe Pro Asp Asp Thr Lys
        115                 120                 125

Leu Thr Lys Ile Glu Thr Leu Arg Phe Ala Tyr Asn Tyr Ile Trp Ala
    130                 135                 140

Leu Ala Glu Thr Leu Arg Leu Ala Asp Gln Gly Leu Pro Gly Gly Ser
145                 150                 155                 160

Ala Arg Glu Arg Leu Leu Pro Pro Gln Cys Val Pro Cys Leu Pro Gly
                165                 170                 175

Pro Pro Ser Pro Ala Ser Asp Thr Glu Ser Trp Gly Ser Gly Ala Ala
            180                 185                 190

Ala Ser Pro Cys Ala Thr Val Ala Ser Pro Leu Ser Asp Pro Ser Ser
        195                 200                 205

Pro Ser Ala Ser Glu Asp Phe Thr Tyr Gly Pro Gly Asp Pro Leu Phe
    210                 215                 220

Ser Phe Pro Gly Leu Pro Lys Asp Leu Leu His Thr Thr Pro Cys Phe
225                 230                 235                 240

Ile Pro Tyr His
```

<210> SEQ ID NO 15
<211> LENGTH: 1312
<212> TYPE: DNA
<213> ORGANISM: Xenopus sp.

<400> SEQUENCE: 15

```
gcgtgtcaca cggcagttgc actcataata cactgtgagc tgacagtcgc aaccacgccc     60
gacagggaac acgcagcaag tctactgcac gactataacc cgacgactcg acccaactca    120
cctgctgctt caggggccaa acaccaagtt ataaagtaag taacttccat tgcaactgca    180
```

```
gcattgtcac ttgcgacagc gcatgaagta gtgagaggca cagaccatgt acatatatgg    240
ggtttgtggt tattatagta agtgggatga tgtttgggtt attatagtaa gtggatgtga    300
agttgtcagt gcaacattgg ggctaaccat tggctgtgtg tttgcgcttg tctaggatgg    360
tgctgctcaa gtgcgagtac cgcgatgaag aggaggacct gacctctgcc tcccctgct    420 ccgtgacctc ctctttccgt tccccggcga cgcagacgtg cagctcggac gatgagcagc    480
tcctgagtcc caccagcccg ggacagcacc agggggaaga aacagcccg cgatgcagga    540 ggagccgagg ccgcgctcag ggcaagagcg gagaaactgt gttaaagatc aagaagaccc    600
ggcgcgttaa agctaacaac cgggaaagga atcgcatgca caacctgaac tctgcgcttg    660
attccctcag ggaagtgttg ccctctttac ctgaagatgc caaactcacc aagatagaga    720
ccttgcgctt tgcctacaac tacatctggg ctcttagcga aactttgcgc cttggcgacc    780
cagtgcaccg atctgcttcc accccagcag cagccatatt ggtgcaggac tcctcttcat    840
cccagagccc ctcctggagc tgcagctcgt ccccttcttc ctcttgttgc tccttctccc    900
cggccagccc tgccagctcc acctcggaca gtattgagtc ctggcagccc tctgagctcc    960
acctgaaccc cttcatgtct gccagcagcg ctttcatttg aactcctgtt ggactatgat   1020
ggattctcac acttccaatt gctacatatg aagaatacct cagtgggggcc ccagtgcaaa   1080 tgattttcct gggaacccag tttattgagc atgagcccat atagtgtaat aatatcatcc   1140
tgcagtgacc aaattgcact ctgtgggttc tgctgatggg gagaagtggg gggcttgatc   1200
cccctgagtt tgtgcttacc tgtatagcat ttactccccc tgctgtcatg cccctggcat   1260
atgatggagt acattgctgg gtctatttta ttatcagcaa tgtgaactga aa           1312

<210> SEQ ID NO 16
<211> LENGTH: 1277
<212> TYPE: DNA
<213> ORGANISM: Xenopus sp.

<400> SEQUENCE: 16
cgagtgcgca acacttgagc tggagtgcgg ggcgcgtgtc acacacacac tgaactgcca     60
ctgacaccag agacacagcg agtgggaacc ccctgctact acaggactag agaaaagcc    120 gcacagcctg cagcgccgca acccgactca cctgctgctc ccggagccac aagcctggcg    180
cacaagatgg tgctgctgaa gtgcgaatac cgcgatgagg tgtcggaact gacctctgtc    240 tcccctgct ccgtgtcctc ctcctcttca cacccgtccc cggcgatgca gacgtgcagc    300
tcggacgatg agcagctaca cagtccgaca agcccgacgc tcacgcacct gcagcaggga    360
cgggaccagg gggaggagaa cagcccgcga tgcaggagga ccgagcccg cggagacacc    420 gtgctgaaga tcaagaagac ccggcgcgtt aaagccaata ccgcgagag gaatcgcatg    480 caccacctga actatgcgct cgattctctg agggaggttc taccgtcatt acccgaagac    540
gccaaactca ccaagataga gaccttgcgc tttgcccaca actacatctg ggctcttagc    600
gaaactttgc gcctggccga ccagctgcac ggatctactt ccaccccagc agcagccata    660
ttggtacagg actcctatcc ttccctgagc ccctcctgga gctgcagctc gtccccatcc    720
tccaactctt gcgactcctt ctcccgacc agccctgcca gctccacctc ggacagtatt    780
gagtactggc agccctctga gctccgcttg aaccccttca tgtctgccct ttgaacgcac    840
aggactatgg gtgattttaa ctttttacac ttttaaattc tgcttcccat aagggtcaag    900
tactgcaggg gttacatatc aagtttacct cagggggggc cacagcaaat tcttttcctg    960
```

```
ggccctaaaa tgtcctctga atttgagccc atatagtgca atggtataac cctgcaatgg    1020
tataatccag caatggtata atcctgcatc gttacctaat tgtactttgt ggggtctgct    1080
gatgggggac aagtgtttga cctgtgtcca gagtttcaca tttactcccc cttttggtat    1140
atctctggcc gcaacacttg ctgtgtctgt ttcatcgtta gctatgtgta ttaggaaact    1200
gtctatccct catctgcacc tgttagacta cagctaccaa cttcctgtta ccaggggct     1260 actgggtaat gtacttc                                                   1277

<210> SEQ ID NO 17
<211> LENGTH: 1385
<212> TYPE: DNA
<213> ORGANISM: Mus musculus
<220> FEATURE:
<221> NAME/KEY: CDS
<222> LOCATION: (382)..(1170)

<400> SEQUENCE: 17
cttaggaagc gccaagcccg cggagcggag gacaccgtgc tcggttccgg gtgggggaca    60
ttcccggaca cacaccggag cagcagctgc gccggaacat tggagccgcg taggtaagtg    120
tgcatgccgc ggcttttccat tcgcaggcag tgtccccacg caggctcacg ccgcccacgc    180
taactccatc gtttagacgc agtgacttct gtgaccggca aaggtggct cgagcccggg     240 gcgctcctcc ccagctctgt cctcgccatc ttcgcgaatg cacattgagg agatggagg    300 gggggggggcg gggcgcggcg ccagcgacac tttaccctgt ccattctggg aataaatttc    360
atctgcctct tctttctcag g atg ttc gtc aaa tct gag act ctg gag ttg     411
                         Met Phe Val Lys Ser Glu Thr Leu Glu Leu
                           1               5                   10 aag gag gaa gag gag gta ctg atg ctg ctg ggc tcg gct tcc ccg gcc     459
Lys Glu Glu Glu Glu Val Leu Met Leu Leu Gly Ser Ala Ser Pro Ala
               15                  20                  25 tcg gcg acc ctg acc ccg atg tcc tcc agc gcg gac gag gag gag gac     507
Ser Ala Thr Leu Thr Pro Met Ser Ser Ser Ala Asp Glu Glu Glu Asp
       30                  35                  40 gag gag ctg cgc cgg ccg ggc tcc gcg cgt ggg cag cgt gga gcg gaa     555
Glu Glu Leu Arg Arg Pro Gly Ser Ala Arg Gly Gln Arg Gly Ala Glu
   45                  50                  55 gcc gag cag ggg gtg cag ggc agt ccg gcg tcg ggt gcc ggg ggt tgc     603
Ala Glu Gln Gly Val Gln Gly Ser Pro Ala Ser Gly Ala Gly Gly Cys
60                  65                  70 cgg cca ggg cgg ctg ctg ggc ctg atg cac gag tgc aag cgt cgc ccg     651
Arg Pro Gly Arg Leu Leu Gly Leu Met His Glu Cys Lys Arg Arg Pro
75                  80                  85                  90 tcg cgc tca cgg gcc gtc tcc cga ggt gcc aag acg gcg gag acg gtg     699
Ser Arg Ser Arg Ala Val Ser Arg Gly Ala Lys Thr Ala Glu Thr Val
               95                 100                 105 cag cgc atc aag aag acc cgc agg ctc aag gcc aac aac cgc gag cgc     747
Gln Arg Ile Lys Lys Thr Arg Arg Leu Lys Ala Asn Asn Arg Glu Arg
       110                 115                 120 aac cgc atg cac aac cta aac gcc gcg ctg gac gcg ctg cgc gag gtg     795
Asn Arg Met His Asn Leu Asn Ala Ala Leu Asp Ala Leu Arg Glu Val
   125                 130                 135 ctg ccc acc ttc ccc gag gat gcc aag ctc acg aag atc gag acg ctg     843
Leu Pro Thr Phe Pro Glu Asp Ala Lys Leu Thr Lys Ile Glu Thr Leu
140                 145                 150 cgc ttc gcc cac aat tac atc tgg gcg ctc acc gag act ctg cgc ctg     891
Arg Phe Ala His Asn Tyr Ile Trp Ala Leu Thr Glu Thr Leu Arg Leu
155                 160                 165                 170
```

```
gcg gac cac tgc gcc ggc gcc ggt ggc ctc cag ggg gcg ctc ttc acg      939
Ala Asp His Cys Ala Gly Ala Gly Gly Leu Gln Gly Ala Leu Phe Thr
            175                 180                 185 gag gcg gtg ctc ctg agc ccg gga gct gcg ctc ggc gcc agc ggg gac      987
Glu Ala Val Leu Leu Ser Pro Gly Ala Ala Leu Gly Ala Ser Gly Asp
        190                 195                 200 agc cct tct cca cct tcc tcc tgg agc tgc acc aac agc ccg gcg tca     1035
Ser Pro Ser Pro Pro Ser Ser Trp Ser Cys Thr Asn Ser Pro Ala Ser
        205                 210                 215 tcc tcc aac tcc acg tcc cca tac agc tgc act tta tcg ccc gct agc     1083
Ser Ser Asn Ser Thr Ser Pro Tyr Ser Cys Thr Leu Ser Pro Ala Ser
    220                 225                 230 ccc ggg tca gac gtg gac tac tgg cag ccc cca cct ccg gag aag cat     1131
Pro Gly Ser Asp Val Asp Tyr Trp Gln Pro Pro Pro Pro Glu Lys His
235                 240                 245                 250 cgt tat gcg cct cac ctg ccc ctc gcc agg gac tgt atc tagagctgcg     1180
Arg Tyr Ala Pro His Leu Pro Leu Ala Arg Asp Cys Ile
                255                 260 ggtctccctc tctcgtctcc tacccgggcc ctccttccca tccttctccc gcccccacc   1240 ctccacgccc cggaatccac ttcacagaac agaagttggc cctttgcaat cccctccgcg   1300
gctggtgctt cggggggttgg aaaacaactc tggtttattg aaattaagat tttggtcaaa   1360
aagaatatgc ttttttggaat tgggg                                        1385

<210> SEQ ID NO 18
<211> LENGTH: 263
<212> TYPE: PRT
<213> ORGANISM: Mus musculus

<400> SEQUENCE: 18

Met Phe Val Lys Ser Glu Thr Leu Glu Leu Lys Glu Glu Glu Glu Val
 1               5                  10                  15

Leu Met Leu Leu Gly Ser Ala Ser Pro Ala Ser Ala Thr Leu Thr Pro
            20                  25                  30

Met Ser Ser Ser Ala Asp Glu Glu Glu Asp Glu Glu Leu Arg Arg Pro
        35                  40                  45

Gly Ser Ala Arg Gly Gln Arg Gly Ala Glu Ala Glu Gln Gly Val Gln
    50                  55                  60

Gly Ser Pro Ala Ser Gly Ala Gly Gly Cys Arg Pro Gly Arg Leu Leu
65                  70                  75                  80

Gly Leu Met His Glu Cys Lys Arg Arg Pro Ser Arg Ser Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Ala Gly
                165                 170                 175

Ala Gly Gly Leu Gln Gly Ala Leu Phe Thr Glu Ala Val Leu Leu Ser
            180                 185                 190

Pro Gly Ala Ala Leu Gly Ala Ser Gly Asp Ser Pro Ser Pro Pro Ser
        195                 200                 205
```

```
Ser Trp Ser Cys Thr Asn Ser Pro Ala Ser Ser Asn Ser Thr Ser
    210                 215                 220
Pro Tyr Ser Cys Thr Leu Ser Pro Ala Ser Pro Gly Ser Asp Val Asp
225                 230                 235                 240
Tyr Trp Gln Pro Pro Pro Glu Lys His Arg Tyr Ala Pro His Leu
                245                 250                 255
Pro Leu Ala Arg Asp Cys Ile
            260

<210> SEQ ID NO 19
<211> LENGTH: 804
<212> TYPE: DNA
<213> ORGANISM: Mus musculus
<220> FEATURE:
<221> NAME/KEY: CDS
<222> LOCATION: (160)..(801)

<400> SEQUENCE: 19
attcttttga gtcgggagaa ctaggtaaca attcggaaac tccaaagggt ggatgagggg       60
cgcgcggggt gtgtgtgggg gatactctgg tcccccgtgc agtgacctct aagtcagagg      120
ctggcacaca cacaccttcc attttttccc aaccgcagg atg gcg cct cat ccc         174
                                            Met Ala Pro His Pro
                                              1               5 ttg gat gcg ctc acc atc caa gtg tcc cca gag aca caa caa cct ttt        222
Leu Asp Ala Leu Thr Ile Gln Val Ser Pro Glu Thr Gln Gln Pro Phe
             10                  15                  20 ccc gga gcc tcg gac cac gaa gtg ctc agt tcc aat tcc acc cca cct        270
Pro Gly Ala Ser Asp His Glu Val Leu Ser Ser Asn Ser Thr Pro Pro
         25                  30                  35 agc ccc act ctc ata cct agg gac tgc tcc gaa gca gaa gtg ggt gac        318
Ser Pro Thr Leu Ile Pro Arg Asp Cys Ser Glu Ala Glu Val Gly Asp
     40                  45                  50 tgc cga ggg acc tcg agg aag ctc cgc gcc cga cgc gga ggg cgc aac        366
Cys Arg Gly Thr Ser Arg Lys Leu Arg Ala Arg Arg Gly Gly Arg Asn
 55                  60                  65 agg ccc aag agc gag ttg gca ctc agc aaa cag cga aga agc cgg cgc        414
Arg Pro Lys Ser Glu Leu Ala Leu Ser Lys Gln Arg Arg Ser Arg Arg
 70                  75                  80                  85 aag aag gcc aat gat cgg gag cgc aat cgc atg cac aac ctc aac tcg        462
Lys Lys Ala Asn Asp Arg Glu Arg Asn Arg Met His Asn Leu Asn Ser
                 90                  95                 100 gcg ctg gat gcg ctg cgc ggt gtc ctg ccc acc ttc ccg gat gac gcc        510
Ala Leu Asp Ala Leu Arg Gly Val Leu Pro Thr Phe Pro Asp Asp Ala
            105                 110                 115 aaa ctt aca aag atc gag acc ctg cgc ttc gcc cac aac tac atc tgg        558
Lys Leu Thr Lys Ile Glu Thr Leu Arg Phe Ala His Asn Tyr Ile Trp
        120                 125                 130 gca ctg act cag acg ctg cgc ata gcg gac cac agc ttc tat ggc ccg        606
Ala Leu Thr Gln Thr Leu Arg Ile Ala Asp His Ser Phe Tyr Gly Pro
    135                 140                 145 gag ccc cct gtg ccc tgt gga gag ctg ggg agc ccc gga ggt ggc tcc        654
Glu Pro Pro Val Pro Cys Gly Glu Leu Gly Ser Pro Gly Gly Gly Ser
150                 155                 160                 165 aac ggg gac tgg ggc tct atc tac tcc cca gtc tcc caa gcg ggt aac        702
Asn Gly Asp Trp Gly Ser Ile Tyr Ser Pro Val Ser Gln Ala Gly Asn
                170                 175                 180 ctg agc ccc acg gcc tca ttg gag gaa ttc cct ggc ctg cag gtg ccc        750
Leu Ser Pro Thr Ala Ser Leu Glu Glu Phe Pro Gly Leu Gln Val Pro
            185                 190                 195
```

```
                                                             -continued agc tcc cca tcc tat ctg ctc ccg gga gca ctg gtg ttc tca gac ttc       798
Ser Ser Pro Ser Tyr Leu Leu Pro Gly Ala Leu Val Phe Ser Asp Phe
        200                 205                 210 ttg tga                                                               804
Leu
```

<210> SEQ ID NO 20
<211> LENGTH: 214
<212> TYPE: PRT
<213> ORGANISM: Mus musculus

<400> SEQUENCE: 20

```
Met Ala Pro His Pro Leu Asp Ala Leu Thr Ile Gln Val Ser Pro Glu
  1               5                  10                  15

Thr Gln Gln Pro Phe Pro Gly Ala Ser Asp His Glu Val Leu Ser Ser
                 20                  25                  30

Asn Ser Thr Pro Pro Ser Pro Thr Leu Ile Pro Arg Asp Cys Ser Glu
             35                  40                  45

Ala Glu Val Gly Asp Cys Arg Gly Thr Ser Arg Lys Leu Arg Ala Arg
         50                  55                  60

Arg Gly Gly Arg Asn Arg Pro Lys Ser Glu Leu Ala Leu Ser Lys Gln
 65                  70                  75                  80

Arg Arg Ser Arg Arg Lys Lys Ala Asn Asp Arg Glu Arg Asn Arg Met
                 85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu
    210
```

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)
<223> OTHER INFORMATION: a, c, g, t, unknown or other

<400> SEQUENCE: 21
cgcggatccm gnaaygarmg bgarm                                            25

<210> SEQ ID NO 22
<211> LENGTH: 26
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (12)
<223> OTHER INFORMATION: a, c, g, t, unknown or other

<400> SEQUENCE: 22
cgcggatccg cnaaygchmg bgarmg                                          26

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccggaattcg tytcvayytt rctvadytt                                       29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccggaattcg tytcvayytt dgavadytt                                       29

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Leu or Met
<220> FEATURE:
<221> NAME/KEY: MOD_RES
<222> LOCATION: (5)
<223> OTHER INFORMATION: Val or Ile

<400> SEQUENCE: 25

Lys Xaa Ser Lys Xaa Glu Thr
 1               5

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)
<223> OTHER INFORMATION: inosine
<220> FEATURE:
<221> NAME/KEY: modified_base
<222> LOCATION: (17)
<223> OTHER INFORMATION: inosine
<220> FEATURE:
<221> NAME/KEY: modified_base
<222> LOCATION: (23)
```

```
<223> OTHER INFORMATION: inosine
<220> FEATURE:
<221> NAME/KEY: modified_base
<222> LOCATION: (29)
<223> OTHER INFORMATION: inosine

<400> SEQUENCE: 26
cgggatccaa ygmnmgngar mgnaaymgnr t                              31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)
<223> OTHER INFORMATION: inosine
<220> FEATURE:
<221> NAME/KEY: modified_base
<222> LOCATION: (17)
<223> OTHER INFORMATION: inosine
<220> FEATURE:
<221> NAME/KEY: modified_base
<222> LOCATION: (23)
<223> OTHER INFORMATION: inosine
<220> FEATURE:
<221> NAME/KEY: modified_base
<222> LOCATION: (26)
<223> OTHER INFORMATION: inosine

<400> SEQUENCE: 27
cggaattcar ngtytcnayy ttnswnadyt t                              31

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Glu or Ala
<220> FEATURE:
<221> NAME/KEY: MOD_RES
<222> LOCATION: (8)
<223> OTHER INFORMATION: Val or Met

<400> SEQUENCE: 28

Asn Xaa Arg Glu Arg Asn Arg Xaa
  1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Asn Glu Arg Glu Arg
  1               5

<210> SEQ ID NO 30
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Ala Asn Ala Arg Glu Arg
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Met or Leu
<220> FEATURE:
<221> NAME/KEY: MOD_RES
<222> LOCATION: (5)
<223> OTHER INFORMATION: Val or Ile

<400> SEQUENCE: 31

Lys Xaa Ser Lys Xaa Glu Thr Leu
  1               5
```

We claim:

1. An isolated polypeptide comprising an amino acid sequence having at least 95% identity to amino acids 82-140 of SEQ ID NO:20, wherein said amino acid sequence forms a basic helix loop helix domain.

2. The isolated polypeptide of claim 1, wherein the amino acid sequence has at least 98% identity to amino acids 82-140 of SEQ ID NO:20.

* * * * *